US008568990B2

(12) United States Patent
Zuker et al.

(10) Patent No.: US 8,568,990 B2
(45) Date of Patent: *Oct. 29, 2013

(54) METHODS FOR IDENTIFYING COMPOUNDS THAT MODULATE SENSORY SIGNALING THROUGH THE TASTE CELL SPECIFIC G-PROTEIN COUPLED RECEPTOR GPCR-B4

(75) Inventors: Charles S. Zuker, San Diego, CA (US); Jon Elliot Adler, Pacific Beach, CA (US); Juergen Lindemeier, Werl (DE)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/290,026

(22) Filed: Nov. 4, 2011

(65) Prior Publication Data
US 2012/0142029 A1    Jun. 7, 2012

Related U.S. Application Data

(60) Continuation of application No. 12/960,409, filed on Dec. 3, 2010, now Pat. No. 8,071,743, which is a division of application No. 11/716,362, filed on Mar. 8, 2007, now Pat. No. 7,863,433, which is a continuation of application No. 10/096,144, filed on Mar. 8, 2002, now Pat. No. 7,282,557, which is a continuation of application No. 09/361,631, filed on Jul. 27, 1999, now Pat. No. 6,383,778.

(60) Provisional application No. 60/095,464, filed on Jul. 28, 1998, provisional application No. 60/112,747, filed on Dec. 17, 1998.

(51) Int. Cl.
*G01N 33/567* (2006.01)

(52) U.S. Cl.
USPC ........................................... 435/7.1; 436/501

(58) Field of Classification Search
None
See application file for complete search history.

(56) References Cited

U.S. PATENT DOCUMENTS

| 4,146,501 A | 3/1979 | Henkin |
| 5,688,662 A | 11/1997 | Margolskee |
| 6,383,778 B1 | 5/2002 | Zuker et al. |
| 2003/0008344 A1 | 1/2003 | Adler et al. |

FOREIGN PATENT DOCUMENTS

| WO | WO 01/86563 A2 | 9/2001 |
| WO | WO 03/004992 A2 | 1/2003 |

OTHER PUBLICATIONS

Abe et al, Primary Structure and Cell-type Specific Expression of a Gustatory G Protein-coupled Receptor Related of Olfactory Receptors, The Journal of Biological Chemistry, 268:(16) 12033-12039, 1993.
Adler et al., "A novel family of mammalian taste receptors," 2000, Cell 100:693-702.
Alexander et al., "Altering the Antigenicity of Proteins," PNAS, vol. 89, pp. 3352-3356, 1992.
Bowie et al, "Deciphering the message in protein sequences: tolerance to amino acid substitutions," 1990, Science 247, 1306-1310.
Brown et al.: "Cloning and characterization of an extracelluar Ca.sup.2+-sensing receptor from bovine parathyroid" Letters to Nature 366: 575-580, 1993.
Cao et al: "Cloning and localization of two multigene receptor families in goldfish olfactory epithelium" Proc. Natl. Acad. Sci. 95 11987-11992, 1998.
Chandrashekar et al., "T2Rs function as bitter taste receptors," Cell 100:703-711, 2000.
Chaudhari et al: "The Taste of Monosodium Glutamate: Membrane Receptors in Taste Buds" Journal of Neurosciene 16(12): 3817-3826, 1996.
Dulac et al.: "A Novel Family of Genes Encoding Putative Pheromone Receptors in Mammals" Cell 83 195-206, 1995.
Guo, H.H. et al.; "Protein tolerance to random amino acid change," PNAS, vol. 101, No. 25, pp. 9205-9210, 2004.
Herrada et al.; "A Novel Family of Putative Pheromone Receptors in Mammals with a Topographically Organized and Sexually Dimorphic Distribution"; Cell 90: 763-773, 1997.
Hoon, Mark A. et al.; "Analysis and Comparison of Partial Sequences of Clones from a Taste-bud enriched cDNA Library"; J. Dent Res. 76: 831-838, 1997.
Hoon, Mark A. et al.; "Putative Mammalian Taste Receptors: A Class of Taste-Specific GPCRs with Distinct Topographic Selectivity"; 1999, *Cell*, vol. 96, pp. 541-551.
Kel, Alexander et al., "A genetic algorithm for designing gene family-specific oligonucleotide sets used for hybridization: the G protein-coupled receptor protein superfamily;" 1998, *Bioinformatics*, vol. 14, No. 3, pp. 259-270.
Kinnamon et al.; "Mechanisms of taste transduction" Current Opinion in Neurobiology 6 506-513, 1996.
Li, Xiaodong et al.; "Human receptors for sweet and umami taste,", PNAS, Apr. 2, 2002, pp. 4692-4696, vol. 99, *National Academy of Sciences*.
Lindermann, B.; Nat. Neuroscience 3(2)99-100, 2000.
Lush, Ian E.; "The genetics of tasting mice" Genet. Res. Camb. 53 95-99, 1989.
Margolskee, Robert F.; "The Molecular Biology of Taste Transduction"; BioEssays, 15:(10) 645-650, 1993.
Matsunami et al.; "A Multigene Family Encoding a Diverse Array of Putative Pheromone Receptors in Mammals"; Cell 90: 775-784, 1997.

(Continued)

*Primary Examiner* — John Ulm
(74) *Attorney, Agent, or Firm* — Morgan, Lewis & Bockius LLP

(57) ABSTRACT

The invention provides isolated nucleic acid and amino acid sequences of sensory cell specific G-protein coupled receptors, antibodies to such receptors, methods of detecting such nucleic acids and receptors, and methods of screening for modulators of sensory cell specific G-protein coupled receptors.

12 Claims, No Drawings

(56) References Cited

OTHER PUBLICATIONS

Max, Marianna et al., "TAS1r3, encoding a new candidate taste receptor, is allelic to the sweet responsiveness locus Sac," *Nature Genetics*, May 2001, pp. 58-63, vol. 28, Nature Publishing Group.

McLaughlin et al.; "Gustducin is a taste-cell-specific G protein closely related to the transducins" Letters to Nature 357 563-569, 1992.

Montmayeur, Jean-Pierre et al., "A candidate taste receptor gene near a sweet taste locus," *Nature Neuroscience*, May 2001, pp. 492-498, vol. 4, No. 5, Nature Publishing Group.

Naito et al.: Putative pheromone receptors $Ca^{2+}$—sensing receptor in Fugu Proc. Natl. Acad. Sci. 95: 5178-5181, 1998.

Nelson, Greg et al., "An amino-acid taste receptor," *Nature*, Feb. 24, 2002, pp. 1-4, advance online publication.

Nelson, Greg et al., "Mammalian Sweet Taste Receptors," *Cell*, Aug. 10, 2001, pp. 381-390, Cell Press.

Ngo et al., "The Protein Folding Problem and Tertiary Structure"; pp. 14-16, 1994.

Rohrer, Daniel K. et al., "G Protein-Coupled Receptors: Functional and Mechanistic Insights Through Altered Gene Expression," 1998, *Physiological Reviews*, vol. 78, No. 1, pp. 381-390, Cell Press.

Ryba et al.; "A New Multigene Family of Putative Pheromone Receptors"; Neuron 19: 371-379, 1997.

Striem et al.: Sweet tastants stimulate adenylate cyclase coupled to GTP-binding protein in rat tongue membranes Biochem 260: 121-126, 1989.

Wells; "Additivity of mutational effects in proteins," Biochemistry 29(8509-8517)1990.

Wong et al.: "Transduction of bitter and sweet taste by gustducin" Letters to Nature 381 796-800, 1996.

METHODS FOR IDENTIFYING COMPOUNDS THAT MODULATE SENSORY SIGNALING THROUGH THE TASTE CELL SPECIFIC G-PROTEIN COUPLED RECEPTOR GPCR-B4

CROSS-REFERENCES TO RELATED APPLICATIONS

This application is a continuation of U.S. application Ser. No. 12/960,409, filed Dec. 3, 2010, now U.S. Pat. No. 8,071,743 which is a divisional of U.S. application Ser. No. 11/716,362 (now U.S. Pat. No. 7,863,433) filed Mar. 8, 2007, which is a continuation of U.S. application Ser. No. 10/096,144 (now U.S. Pat. No. 7,282,557) filed Mar. 8, 2002, which is a continuation of U.S. application Ser. No. 09/361,631 (now U.S. Pat. No. 6,383,778) filed Jul. 27, 1999, which claims priority to U.S. Application Ser. No. 60/095,464, filed Jul. 28, 1998, and U.S. Application Ser. No. 60/112,747, filed Dec. 17, 1998, herein incorporated by reference in their entireties.

STATEMENT AS TO FEDERALLY SPONSORED RESEARCH AND DEVELOPMENT

This invention was made with government support under Grant No. 5R01 DC03160, awarded by the National Institutes of Health. The government has certain rights in this invention.

FIELD OF THE INVENTION

The invention provides isolated nucleic acid and amino acid sequences of sensory cell specific G-protein coupled receptors, antibodies to such receptors, methods of detecting such nucleic acids and receptors, and methods of screening for modulators of sensory cell specific G-protein coupled receptors.

BACKGROUND OF THE INVENTION

Taste transduction is one of the most sophisticated forms of chemotransduction in animals (see, e.g., Margolskee, *BioEssays*. 15:645-650 (1993); Avenet & Lindemann, *J. Membrane Biol.* 112:1-8 (1989)). Gustatory signaling is found throughout the animal kingdom, from simple metazoans to the most complex of vertebrates; its main purpose is to provide a reliable signaling response to non-volatile ligands. Each of these modalities is though to be mediated by distinct signaling pathways mediated by receptors or channels, leading to receptor cell depolarization, generation of a receptor or action potential, and release of neurotransmitter at gustatory afferent neuron synapses (see, e.g., Roper, *Ann. Rev. Neurosci.* 12:329-353 (1989)).

Mammals are believed to have five basic taste modalities: sweet, bitter, sour, salty and unami (the taste of monosodium glutamate) (see, e.g., Kawamura & Kare, *Introduction to Unami: A Basic Taste* (1987); Kinnamon & Cummings, *Ann. Rev. Physiol.* 54:715-731 (1992); Lindemann, *Physiol. Rev.* 76:718-766 (1996); Stewart et al., *Am. J. Physiol.* 272:1-26 (1997)). Extensive psychophysical studies in humans have reported that different regions of the tongue display different gustatory preferences (see, e.g., Hoffmann, *Menchen. Arch. Path. Anat. Physiol.* 62:516-530 (1875); Bradley et al., *Anatomical Record* 212: 246-249 (1985); Miller & Reedy, *Physiol. Behav.* 47:1213-1219 (1990)). Also, numerous physiological studies in animals have shown that taste receptor cells may selectively respond to different tastants (see, e.g., Akabas et al., *Science* 242:1047-1050 (1988); Gilbertson et al., *J. Gen. Physiol.* 100:803-24 (1992); Bernhardt et al., *J. Physiol.* 490:325-336 (1996); Cummings et al., *J. Neurophysiol.* 75:1256-1263 (1996)).

In mammals, taste receptor cells are assembled into taste buds that are distributed into different papillae in the tongue epithelium. Circumvallate papillae, found at the very back of the tongue, contain hundreds (mice) to thousands (human) of taste buds and are particularly sensitive to bitter substances. Foliate papillae, localized to the posterior lateral edge of the tongue, contain dozens to hundreds of taste buds and are particularly sensitive to sour and bitter substances. Fungiform papillae containing a single or a few taste buds are at the front of the tongue and are thought to mediate much of the sweet taste modality.

Each taste bud, depending on the species, contain 50-150 cells, including precursor cells, support cells, and taste receptor cells (see, e.g., Lindemann, *Physiol. Rev.* 76:718-766 (1996)). Receptor cells are innervated at their base by afferent nerve endings that transmit information to the taste centers of the cortex through synapses in the brain stem and thalamus. Elucidating the mechanisms of taste cell signaling and information processing is critical for understanding the function, regulation, and "perception" of the sense of taste.

Although much is known about the psychophysics and physiology of taste cell function, very little is known about the molecules and pathways that mediate these sensory signaling responses (reviewed by Gilbertson, *Current Opn. in Neurobiol.* 3:532-539 (1993)). Electrophysiological studies suggest that sour and salty tastants modulate taste cell function by direct entry of $H^+$ and $Na^+$ ions through specialized membrane channels on the apical surface of the cell. In the case of sour compounds, taste cell depolarization is hypothesized to result from $H^+$ blockage of $K^+$ channels (see, e.g., Kinnamon et al., *Proc. Nat'l Acad. Sci. USA* 85: 7023-7027 (1988)) or activation of pH-sensitive channels (see, e.g., Gilbertson et al., *J. Gen. Physiol.* 100:803-24 (1992)); salt transduction may be partly mediated by the entry of $Na^+$ via amiloride-sensitive channels (see, e.g., Heck et al., *Science* 223:403-405 (1984); Brand et al., *Brain Res.* 207-214 (1985); Avenet et al., *Nature* 331: 351-354 (1988)).

Sweet, bitter, and unami transduction are believed to be mediated by G-protein-coupled receptor (GPCR) signaling pathways (see, e.g., Striem et al., *Biochem.* 260:121-126 (1989); Chaudhari et al., *J. Neuros.* 16:3817-3826 (1996); Wong et al., *Nature* 381: 796-800 (1996)). Confusingly, there are almost as many models of signaling pathways for sweet and bitter transduction as there are effector enzymes for GPCR cascades (e.g., G protein subunits, cGMP phosphodiesterase, phospholipase C, adenylate cyclase; see, e.g., Kinnamon & Margolskee, *Curr. Opin. Neurobiol.* 6:506-513 (1996)). However, little is known about the specific membrane receptors involved in taste transduction, or many of the individual intracellular signaling molecules activated by the individual taste transduction pathways. Identification of such molecules is important given the numerous pharmacological and food industry applications for bitter antagonists, sweet agonists, and modulators of salty and sour taste.

The identification and isolation of taste receptors (including taste ion channels), and taste signaling molecules, such as G-protein subunits and enzymes involved in signal transduction, would allow for the pharmacological and genetic modulation of taste transduction pathways. For example, availability of receptor and channel molecules would permit the screening for high affinity agonists, antagonists, inverse agonists, and modulators of taste cell activity. Such taste modulating compounds could then be used in the pharmaceutical and food industries to customize taste, in addition, such taste cell specific molecules can serve as invaluable tools in the generation of taste topographic maps that elucidate the relationship between the taste cells of the tongue and taste sensory neurons leading to taste centers in the brain.

SUMMARY OF THE INVENTION

The present invention thus provides for the first time nucleic acids encoding a taste cell specific G-protein coupled receptor. These nucleic acids and the polypeptides that they encode are referred to as "GPCR-B4" for G-protein coupled receptor ("GPCR") 84. These taste cell specific GPCRs are components of the taste transduction pathway.

In one aspect, the present invention provides an isolated nucleic acid encoding a sensory transduction G-protein coupled receptor, the receptor comprising greater than about 70% amino acid identity to an amino acid sequence of SEQ ID NO:1, SEQ ID NO:2, or SEQ ID NO:7.

In one embodiment, the nucleic acid comprises a nucleotide sequence of SEQ ID NO:3, SEQ ID NO:4, or SEQ ID NO:8. In another embodiment, the nucleic acid is amplified by primers that selectively hybridize under stringent hybridization conditions to the sane sequence as degenerate primer sets encoding amino acid sequences selected from the group consisting of: SAGGPMCFLM (SEQ ID NO:5) and WMRYHGPYVF (SEQ ID NO:6).

In another aspect, the present invention provides an isolated nucleic acid encoding a sensory transduction G-protein coupled receptor, wherein the nucleic acid specifically hybridizes under highly stringent conditions to a nucleic acid having the sequence of SEQ ID NO:3, SEQ ID NO:4, or SEQ ID NO:8.

In another aspect, the present invention provides an isolated nucleic acid encoding a sensory transduction G-protein coupled receptor, the receptor comprising greater than about 70% amino acid identity to a polypeptide having a sequence of SEQ ID NO:1, SEQ ID NO:2, or SEQ ID NO:7, wherein the nucleic acid selectively hybridizes under moderately stringent hybridization conditions to a nucleotide sequence of SEQ ID NO:3, SEQ ID NO:4, or SEQ ID NO:8.

In another aspect, the present invention provides an isolated nucleic acid encoding an extracellular domain of a sensory transduction G-protein coupled receptor, the extracellular domain having greater than about 70% amino acid sequence identity to the extracellular domain of SEQ ID NO:1.

In another aspect, the present invention provides an isolated nucleic acid encoding a transmembrane domain of a sensory transduction G-protein coupled receptor, the transmembrane domain comprising greater than about 70% amino acid sequence identity to the transmembrane domain of SEQ ID NO: 1.

In another aspect, the present invention provides an isolated sensory transduction G-protein coupled receptor, the receptor comprising greater than about 70% amino acid sequence identity to an amino acid sequence of SEQ ID NO:1, SEQ ID NO:2, or SEQ NO:7.

In one embodiment, the receptor specifically binds to polyclonal antibodies generated against SEQ ID NO:1, SEQ ID NO:2, or SEQ ID NO:7. In another embodiment, the receptor has G-protein coupled receptor activity. In another embodiment, the receptor has an amino acid sequence of SEQ ID NO:1, SEQ ID NO:2, or SEQ ID NO:7. In another embodiment, the receptor is from a human, a rat, or a mouse.

In one aspect, the present invention provides an isolated polypeptide comprising an extracellular domain of a sensory transduction G-protein coupled receptor, the extracellular domain comprising greater than about 70% amino acid sequence identity to the extracellular domain of SEQ ID NO:1.

In one embodiment, the polypeptide encodes the extracellular domain of SEQ ID NO:1. In another embodiment, the extracellular domain is covalently linked to a heterologous polypeptide, forming a chimeric polypeptide.

In one aspect, the present invention provides an isolated polypeptide comprising a transmembrane domain of a sensory transduction G-protein coupled receptor, the transmembrane domain comprising greater than about 70% amino acid sequence identity to the transmembrane domain of SEQ ID NO:1.

In one embodiment, the polypeptide encodes the transmembrane domain of SEQ ID NO:1. In another embodiment, the polypeptide further comprises a cytoplasmic domain comprising greater than about 70% amino acid identity to the cytoplasmic domain of SEQ ID NO:1. In another embodiment, the polypeptide encodes the cytoplasmic domain of SEQ ID NO:1. In another embodiment, the transmembrane domain is covalently linked to a heterologous polypeptide, forming a chimeric polypeptide. In another embodiment, the chimeric polypeptide has G-protein coupled receptor activity.

In one aspect, the present invention provides an antibody that selectively binds to the receptor comprising greater than about 70% amino acid sequence identity to an amino acid sequence of SEQ ID NO:1, SEQ ID NO:2, or SEQ ID NO:7.

In another aspect, the present invention provides an expression vector comprising a nucleic acid encoding a polypeptide comprising greater than about 70% amino acid sequence identity to an amino acid sequence of SEQ ID NO:1, SEQ ID NO:2, or SEQ ID NO:7.

In another aspect, the present invention provides a host cell transfected with the expression vector.

In another aspect, the present invention provides a method for identifying a compound that modulates sensory signaling in sensory cells, the method comprising the steps of: (i) contacting the compound with a polypeptide comprising an extracellular domain of a sensory transduction G-protein coupled receptor, the extracellular domain comprising greater than about 70% amino acid sequence identity to the extracellular domain of SEQ ID NO:1, SEQ ID NO:2, or SEQ ID NO:7; and (ii) determining the functional effect of the compound upon the extracellular domain.

In another aspect, the present invention provides a method for identifying a compound that modulates sensory signaling in sensory cells, the method comprising the steps of: (i) contacting the compound with a polypeptide comprising an extracellular domain of a sensory transduction G-protein coupled receptor, the transmembrane domain comprising greater than about 70% amino acid sequence identity to the extracellular domain of SEQ ID NO:1, SEQ ID NO:2, or SEQ ID NO:7; and (ii) determining the functional effect of the compound upon the transmembrane domain.

In one embodiment, the polypeptide is a sensory transduction G-protein coupled receptor, the receptor comprising greater than about 70% amino acid identity to a polypeptide encoding SEQ ID NO:1, SEQ ID NO:2, or SEQ ID NO:7. In another embodiment, polypeptide comprises an extracellular domain that is covalently linked to a heterologous polypeptide, forming a chimeric polypeptide. In another embodiment, the polypeptide has G-protein coupled receptor activity. In another embodiment, the extracellular domain is linked to a solid phase, either covalently or non-covalently. In another embodiment, the functional effect is determined by measuring changes in intracellular cAMP, IP3, or $Ca^{2+}$. In another embodiment, the functional effect is a chemical effect. In another embodiment, the functional effect is a chemical effect. In another embodiment, the functional effect is determined by measuring binding of the compound to the extracellular domain. In another embodiment, the polypeptide is recombinant. In another embodiment, the polypeptide is expressed in a cell or cell membrane. In another embodiment, the cell is a eukaryotic cell.

In one embodiment, the polypeptide comprises an transmembrane domain that is covalently linked to a heterologous polypeptide, forming a chimeric polypeptide.

In one aspect, the present invention provides a method of making a sensory transduction G-protein coupled receptor, the method comprising the step of expressing the receptor from a recombinant expression vector comprising a nucleic acid encoding the receptor, wherein the amino acid sequence of the receptor comprises greater than about 70% amino acid identity to a polypeptide having a sequence of SEQ NO:1, SEQ ID NO:2, or SEQ ID NO:7.

In one aspect, the present invention provides a method of making a recombinant cell comprising a sensory transduction G-protein coupled receptor, the method comprising the step of transducing the cell with an expression vector comprising a nucleic acid encoding the receptor, wherein the amino acid sequence of the receptor comprises greater than about 70% amino acid identity to a polypeptide having a sequence of SEQ ID NO:1, SEQ ID NO:2, or SEQ ID NO:7.

In one aspect, the present invention provides a method of making an recombinant expression vector comprising a nucleic acid encoding a sensory transduction G-protein coupled receptor, the method comprising the step of ligating to an expression vector a nucleic acid encoding the receptor, wherein the amino acid sequence of the receptor comprises greater than about 70% amino acid identity to a polypeptide having a sequence of SEQ ID NO:1, SEQ ID NO:2, or SEQ ID NO:7.

BRIEF DESCRIPTION OF THE DRAWINGS

Not applicable.

DETAILED DESCRIPTION OF THE INVENTION

I. Introduction

The present invention provides for the first time nucleic acids encoding a taste cell specific G-protein coupled receptor. These nucleic acids and the receptors that they encode are referred to as "GPCR" for G-protein coupled receptor, and are designated as GPCR-B4. These taste cell specific GPCR are components of the taste transduction pathway (see, e.g., Example II). These nucleic acids provide valuable probes for the identification of taste cells, as the nucleic acids are specifically expressed in taste cells. For example, probes for GPCR polypeptides and proteins can be used to identity subsets of taste cells such as foliate cells and circumvallate cells, or specific taste receptor cells, e.g., sweet, sour, salty, and bitter. They also serve as tools for the generation of taste topographic maps that elucidate the relationship between the taste cells of the tongue and taste sensory neurons leading to taste centers in the brain. Furthermore, the nucleic acids and the proteins they encode can be used as probes to dissect taste-induced behaviors.

The invention also provides methods of screening for modulators, e.g., activators, inhibitors, stimulators, enhancers, agonists, and antagonists, of these novel taste cell GPCRs. Such modulators of taste transduction are useful for pharmacological and genetic modulation of taste signaling pathways. These methods of screening can be used to identify high affinity agonists and antagonists of taste cell activity. These modulatory compounds can then be used in the food and pharmaceutical industries to customize taste. Thus, the invention provides assays for taste modulation, where GPCR-B4 acts as an direct or indirect reporter molecule for the effect of modulators on taste transduction. GPCRs can be used in assays, e.g., to measure changes in ion concentration, membrane potential, current flow, ion flux, transcription, signal transduction, receptor-ligand interactions, second messenger concentrations, in vitro, in vivo, and ex vivo. In one embodiment, GPCR-B4 can be used as an indirect reporter via attachment to a second reporter molecule such as green fluorescent protein (see, e.g., Mistili & Spector, *Nature Biotechnology* 15:961-964 (1997)). In another embodiment, GPCR B-4-s are recombinantly expressed in cells, and modulation of taste transduction via GPCR activity is assayed by measuring changes in $Ca^{2+}$ levels (see Example II).

Methods of assaying for modulators of taste transduction include in vitro ligand binding assays using GPCR-B4, portions thereof such as the extracellular domain, or chimeric proteins comprising one or more domains of GPCR-B4, oocyte GPCR-B4 expression; tissue culture cell GPCR-B4 expression; transcriptional activation of GPCR-B4; phosphorylation and dephosphorylation of GPCRs; G-protein binding to GPCRs; ligand binding assays; voltage, membrane potential and conductance changes; ion flux assays; changes in intracellular second messengers such as cAMP and inositol triphosphate; changes in intracellular levels; and neurotransmitter release.

Finally, the invention provides for methods of detecting GPCR-B4 nucleic acid and protein expression, allowing investigation of taste transduction regulation and specific identification of taste receptor cells. GPCR-B4 also provides useful nucleic acid probes for paternity and forensic investigations. GPCR-B4 is useful as a nucleic acid probe for identifying subpopulations of taste receptor cells such as foliate, fungiform, and circumvallate taste receptor cells. GPCR-B4 receptors can also be used to generate monoclonal and polyclonal antibodies useful for identifying taste receptor cells. Taste receptor cells can be identified using techniques such as reverse transcription and amplification of mRNA, isolation of total RNA or poly $A^+$ RNA, northern blotting, dot blotting, in situ hybridization, RNase protection, S1 digestion, probing DNA microchip arrays, western blots, and the like.

Functionally, GPCR-B4 represents a seven transmembrane G-protein coupled receptor involved in taste transduction, which interacts with a G-protein to mediate taste signal transduction (see, e.g., Fong, *Cell Signal* 8:217 (1996); Baldwin, *Curr. Opin. Cell Biol.* 6:180 (1994)).

Structurally, the nucleotide sequence of GPCR-B4 (see, e.g., SEQ ID NOS:3-4 and 8, isolated from rat, mouse, and human respectively) encodes a polypeptide of approximately 842 amino acids with a predicted molecular weight of approximately 97 kDa and a predicted range of 92-102 kDa (see, e.g., SEQ ID NOS:1-2 and 7, isolated from rat, mouse, and human). Related GPCR-B4 genes from other species share at least about 70% amino acid identity over a amino acid region at least about 25 amino acids in length, optionally 50 to 100 amino acids in length. GPCR-B4 is specifically expressed in foliate and fungiform cells, with lower expression in circumvallate taste receptor cells of the tongue. GPCR-B4 is an moderately rare sequence found in approximately 1/150,000 cDNAs from an oligo-dT primed circumvallate cDNA library (see Example I).

The present invention also provides polymorphic variants of the GPCR-B4 depicted in SEQ ID NO:1: variant #1, in which an isoleucine residue is substituted for a leucine acid residue at amino acid position 8; variant #2, in which an aspartic acid residue is substituted for a glutamic acid residue at amino acid position 26; and variant #3, in which a glycine residue is substituted for an alanine residue at amino acid position 46.

Specific regions of the GPCR-B4 nucleotide and amino acid sequence may be used to identify polymorphic variants, interspecies homologs, and alleles of GPCR-B4. This identification can be made in vitro, e.g., under stringent hybridization conditions or PCR (using primers encoding SEQ ID NOS:5-6) and sequencing, or by using the sequence information in a computer system for comparison with other nucleotide sequences. Typically, identification of polymorphic variants and alleles of GPCR-B4 is made by comparing an amino acid sequence of about 25 amino acids or more, e.g., 50-100 amino acids. Amino acid identity of approximately at least 70% or above, optionally 80% or 90-95% or above typically demonstrates that a protein is a polymorphic variant, interspecies homolog, or allele of GPCR-B4. Sequence comparison can be performed using any of the sequence comparison algorithms discussed below. Antibodies that bind specifically to GPCR-B4 or a conserved region thereof can also be used to identify alleles, interspecies homologs, and polymorphic variants.

Polymorphic variants, interspecies homologs, and alleles of GPCR B4 are confirmed by examining taste cell specific expression of the putative GPCR-B4 polypeptide. Typically, GPCR-B4 having the amino acid sequence of SEQ ID NO:1-2 or 7 is used as a positive control in comparison to the putative GPCR-B4 protein to demonstrate the identification of a polymorphic variant or allele of GPCR-B4. The polymorphic variants, alleles and interspecies homologs are expected to retain the seven transmembrane structure of a G-protein coupled receptor.

GPCR-B4 nucleotide and amino acid sequence information may also be used to construct models of taste cell specific polypeptides in a computer system. These models are subsequently used to identify compounds that can activate or inhibit GPCR B4. Such compounds that modulate the activity of GPCR B4 can be used to investigate the role of GPCR-B4 in taste transduction.

The isolation of GPCR-B4 for the first time provides a means for assaying for inhibitors and activators of G-protein coupled receptor taste transduction. Biologically active GPCR-B4 is useful for testing inhibitors and activators of GPCR-B4 as taste transducers using in vivo and in vitro expression that measure, e.g., transcriptional activation of GPCR-B4; ligand binding; phosphorylation and dephosphorylation; binding to G-proteins; G-protein activation; regulatory molecule binding; voltage, membrane potential and conductance changes; ion flux; intracellular second messengers such as cAMP and inositol triphosphate; intracellular calcium levels; and neurotransmitter release. Such activators and inhibitors identified using GPCR-B4, can be used to further study taste transduction and to identify specific taste agonists and antagonists. Such activators and inhibitors are useful as pharmaceutical and food agents for customizing taste.

Methods of detecting GPCR B4 nucleic acids and expression of GPCR-B4 are also useful for identifying taste cells and creating topological maps of the tongue and the relation of tongue taste receptor cells to taste sensory neurons in the brain. Chromosome localization of the genes encoding human GPCR-B4 can be used to identify diseases, mutations, and traits caused by and associated with GPCR-B4.

II. Definitions

As used herein, the following terms have the meanings ascribed to them unless specified otherwise.

"Taste receptor cells" are neuroepithelial cells that are organized into groups to form taste buds of the tongue, e.g., foliate, fungiform, and circumvallate cells (see, e.g., Roper et al., *Ann. Rev. Neurosci.* 12:329-353 (1989)).

"GPCR-B4," also called "TR2," refers to a G-protein coupled receptor that is specifically expressed in taste receptor cells such as foliate, fungiform, and circumvallate cells (see, e.g., Hoon et al., *Cell* 96:541-551 (1999), herein incorporated by reference in its entirety). Such taste cells can be identified because they express specific molecules such as Gustducin, a taste cell specific G protein (McLaughlin et al., *Nature* 357:563-569 (1992)). Taste receptor cells can also be identified on the basis of morphology (see, e.g., Roper, supra). GPCR-B4 has the ability to act as a receptor for taste transduction, as described in Example II.

GPCR-B4 encodes GPCRs with seven transmembrane regions that have "G-protein coupled receptor activity," e.g., they bind to G-proteins in response to extracellular stimuli and promote production of second messengers such as IP3, cAMP, and $Ca^{2+}$ via stimulation of enzymes such as phospholipase C and adenylate cyclase (for a description of the structure and function of GPCRs, see, e.g., Fong, supra, and Baldwin, supra).

The term GPCR-B4 therefore refers to polymorphic variants, alleles, mutants, and interspecies homologs that: (1) have about 70% amino acid sequence identity, optionally about 75, 80, 85, 90, or 95% amino acid sequence identity to SEQ ID NOS:1-2 and 7 over a window of about 25 amino acids, optionally 50-100 amino acids; (2) bind to antibodies raised against an immunogen comprising an amino acid sequence selected from the group consisting of SEQ ID NO:1-2 and 7 and conservatively modified variants thereof; (3) specifically hybridize (with a size of at least about 500, optionally at least about 900 nucleotides) under stringent hybridization conditions to a sequence selected from the group consisting of SEQ NO:3-4 and 8, and conservatively modified variants thereof; or (4) are amplified by primers that specifically hybridize under stringent hybridization conditions to the same sequence as a degenerate primer sets encoding SEQ ID NOS:5-6.

Topologically, sensory GPCRs have an N-terminal "extracellular domain," a "transmembrane domain" comprising seven transmembrane regions and corresponding cytoplasmic and extracellular loops, and a C-terminal "cytoplasmic domain" (see, e.g., Hoon et al., *Cell* 96:541-551 (1999); Buck & Axel, *Cell* 65:175-187 (1991)). These domains can be structurally identified using methods known to those of skill in the art, such as sequence analysis programs that identify hydrophobic and hydrophilic domains (see, e.g., Kyte & Doolittle, *J. Mal. Biol.* 157:105-132 (1982)). Such domains are useful for making chimeric proteins and for in vitro assays of the invention.

"Extracellular domain" therefore refers to the domain of GPCR-B4 that protrudes from the cellular membrane and binds to extracellular ligand. This region starts at the N-terminus and ends approximately at the conserved glutamic acid at amino acid position 563 plus or minus approximately 20 amino acids. The region corresponding to amino acids 1-580 of SEQ ID NO:1 (nucleotides 1-1740, with nucleotide 1 starting at the ATG initiator methionine codon) is one embodiment of an extracellular domain that extends slightly into the transmembrane domain. This embodiment is useful for in vitro ligand binding assays, both soluble and solid phase.

"Transmembrane domain," comprising seven transmembrane regions plus the corresponding cytoplasmic and extracellular loops, refers to the domain of GPCR-B4 that starts approximately at the conserved glutamic acid residue at amino acid position 563 plus or minus approximately 20 amino acids and ends approximately at the conserved tyrosine amino acid residue at position 812 plus or minus approximately 10 amino acids.

"Cytoplasmic domain" refers to the domain of GPCR-134 that starts at the conserved tyrosine amino acid residue at position 812 plus or minus approximately 10 amino acids and continues to the C-terminus of the polypeptide.

"Biological sample" as used herein is a sample of biological tissue or fluid that contains GPCR-B4 or nucleic acid encoding GPCR-B4 protein. Such samples include, but are not limited to, tissue isolated from humans, mice, and rats, in particular, ton. Biological samples may also include sections of tissues such as frozen sections taken for histological purposes. A biological sample is typically obtained from a eukaryotic organism, such as insects, protozoa, birds, fish, reptiles, and preferably a mammal such as rat, mouse, cow, dog, guinea pig, or rabbit, and most preferably a primate such as chimpanzees or humans. Tissues include tongue tissue, isolated taste buds, and testis tissue.

"GPCR activity" refers to the ability of a GPCR ter transduce a signal. Such activity can be measured in a heterologous cell, by coupling a GPCR (or a chimeric GPCR) to either a G-protein or promiscuous G-protein such as G$\alpha$15, and an enzyme such as PLC, and measuring increases in intracellular calcium using (Offermans & Simon, *J. Biol. Chem.* 270: 15175-15180 (1995)). Receptor activity can be effectively measured by recording ligand-induced changes in $[Ca^{2+}]_i$ using fluorescent $Ca^{2+}$-indicator dyes and fluorometric imaging. Optionally, the polypeptides of the invention are involved in sensory transduction, optionally taste transduction in taste cells.

The phrase "functional effects" in the context of assays for testing compounds that modulate GPCR-B4 mediated taste transduction includes the determination of any parameter that is indirectly or directly under the influence of the receptor, e.g., functional, physical and chemical effects. It includes ligand binding, changes in ion flux, membrane potential, current flow, transcription, G-protein binding, GPCR phosphorylation or dephosphorylation, signal transduction, receptor-ligand interactions, second messenger concentrations (e.g., cAMP, IP3, or intracellular $Ca^{2+}$), in vitro, in vivo, and ex vivo and also includes other physiologic effects such increases or decreases of neurotransmitter or hormone release.

By "determining the functional effect" is meant assays for a compound that increases or decreases a parameter that is indirectly or directly under the influence of GPCR-B4, e.g., functional, physical and chemical effects. Such functional effects can be measured by any means known to those skilled in the art, e.g., changes in spectroscopic characteristics (e.g., fluorescence, absorbance, refractive index), hydrodynamic (e.g., shape), chromatographic, or solubility properties, patch clamping, voltage-sensitive dyes, whole cell currents, radioisotope efflux, inducible markers, oocyte GPCR-B4 expression; tissue culture cell GPCR-B4 expression; transcriptional activation of GPCR-B4; ligand binding assays; voltage, membrane potential and conductance changes; ion flux assays; changes in intracellular second messengers such as cAMP and inositol triphosphate (IP3); changes in intracellular calcium levels; neurotransmitter release, and the like.

"Inhibitors," "activators," and "modulators" of GPCR-B4 are used interchangeably to refer to inhibitory, activating, or modulating molecules identified using in vitro and in vivo assays for taste transduction, e.g., ligands, agonists, antagonists, and their homologs and mimetics. Inhibitors are compounds that, e.g., bind to, partially or totally block stimulation, decrease, prevent, delay activation, inactivate, desensitize, or down regulate taste transduction, e.g., antagonists. Activators are compounds that, e.g., bind to, stimulate, increase, open, activate, facilitate, enhance activation, sensitize or up regulate taste transduction, e.g., agonists. Modulators include compounds that, e.g., alter the interaction of a receptor with: extracellular proteins that bind activators or inhibitor (e.g., ebnerin and other members of the hydrophobic carrier family); G-proteins; kinases (e.g., homologs of rhodopsin kinase and beta adrenergic receptor kinases that are involved in deactivation and desensitization of a receptor); and arrestin-like proteins, which also deactivate and desensitize receptors. Modulators include genetically modified versions of GPCR-B4, e.g., with altered activity, as well as naturally occurring and synthetic ligands, antagonists, agonists, small chemical molecules and the like. Such assays for inhibitors and activators include, e.g., expressing GPCR-B4 in cells or cell membranes, applying putative modulator compounds, and then determining the functional effects on taste transduction, as described above. Samples or assays comprising GPCR-B4 that are treated with a potential activator, inhibitor, or modulator are compared to control samples without the inhibitor, activator, or modulator to examine the extent of inhibition. Control samples (untreated with inhibitors) are assigned a relative GPCR-B4 activity value of 100%. Inhibition of GPCR-B4 is achieved when the GPCR-B4 activity value relative to the control is about 80%, optionally 50% or 25-0%. Activation of GPCR-B4 is achieved when the GPCR-B4 activity value relative to the control is 110%, optionally 150%, optionally 200-500%, or 1000-3000% higher.

"Biologically active" GPCR-B4 refers to GPCR-B4 having GPCR activity as described above, involved in taste transduction in taste receptor cells.

The terms "isolated" "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated GPCR-B4 nucleic acid is separated from open reading frames that flank the GPCR-B4 gene and encode proteins other than GPCR-B4. The term "purified" denotes that a nucleic acid or protein gives rise to essentially one band in an electrophoretic gel. Particularly, it means that the nucleic acid or protein is at least 85% pure, optionally at least 95% pure, and optionally at least 99% pure.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batter et al., *Nucleic Acid Res.* 19:5081 (1991); Ohtsuka et al., *J. Biol. Chem.* 260:2605-2608 (1985); Rossolini et al., *Mol. Cell. Probes* 8:9198 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The ten/is apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUD Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (F);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

Macromolecular structures such as polypeptide structures can be described in terms of various levels of organization, For a general discussion of this organization, see, e.g., Alberts et al., *Molecular Biology of the Cell* ($3^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" or a "detectable moiety" is a composition detectable by spectroscopic, photochemical, biochemical, immunochemical, or chemical means. For example, useful labels include $^{32}P$, fluorescent dyes, electron-dense reagents, enzymes (e.g., as commonly used in an ELISA), biotin, digoxigenin, or haptens and proteins for which ant or 7 can be made detectable, e.g., by incorporating a radiolabel into the peptide, and used to detect antibodies specifically reactive with the peptide).

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are optionally directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed et all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "identical" or percent "identity," in the context of two or more nucleic acids or polypeptide sequences, refer to two or more sequences or subsequences that are the same or have a specified percentage of amino acid residues or nucleotides that are the same (i.e., 70% identity, optionally 75%, 80%, 85%, 90%, or 95% identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Optionally, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad Sci. USA* 85:2444 (1988), by computerized implementations of these algorithms (GAP, BESTFIT, PASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351-360 (1987). The method used is similar to the method described by Higgins & Sharp, *CABIOS* 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395 (1984).

Another example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215: 403-41 0 (1990) respectively. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci.* USA 89:10915 (1989)) alignments (B) of 50, expectation (E) of 10,of M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified, as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)', a dimer of Fab which itself is a light chain joined to $V_H$—$C_H 1$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

For preparation of monoclonal or polyclonal antibodies, any technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy* (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al. *Nature* 348:552-554 (1990); Marks et al, *Biotechnology* 10:779-783 (1992)).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

An "anti-GPCR-B4" antibody is an antibody or antibody fragment that specifically binds a polypeptide encoded by the GPCR-B4 gene, cDNA, or a subsequence thereof.

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to GPCR-B4 from specific species such as rat, mouse, or human can be selected to obtain only those polyclonal antibodies that are specifically immunoreactive with GPCR-B4 and not with other proteins, except for polymorphic variants and alleles of GPCR-B4. This selection may be achieved by subtracting out antibodies that cross-react with GPCR-B4 molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind to a protein, as defined above.

By "host cell" is meant a cell that contains an expression vector and supports the replication or expression of the expression vector. Host cells may be prokaryotic cells such as *E. coli*, or eukaryotic cells such as yeast, insect, amphibian, or mammalian cells such as CHO, HeLa and the like, e.g., cultured cells, explants, and cells in vivo.

III. Isolation of the nucleic acid encoding GPCR-B4

A. General Recombinant DNA Methods

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859-1862 (1981), using an automated synthesizer, as described in Van Devanter et. al., *Nucleic Acids Res.* 12:6159-6168 (1984), Purification of oligonucleotides is by either native acrylamide gel electrophoresis or by anion-exchange HPLC as described in Pearson & Reanier, *J. Chrom.* 255:137-149 (1983).

The sequence of the cloned genes and synthetic oligonucleotides can be verified after cloning using, e.g., the chain termination method for sequencing double-stranded templates of Wallace et al., *Gene* 16:21-26 (1981).

B. Cloning Methods for the Isolation of Nucleotide Sequences Encoding GPCR-B4

In general, the nucleic acid sequences encoding GPCR-B4 and related nucleic acid sequence homologs are cloned from cDNA and genomic DNA libraries by hybridization with a probe, or isolated using amplification techniques with oligonucleotide primers. For example, GPCR-B4 sequences are typically isolated from mammalian nucleic acid (genomic or cDNA) libraries by hybridizing with a nucleic acid probe, the sequence of which can be derived from SEQ ID NOS:3-4 and 8. A suitable tissue from which GPCR-B4 RNA and cDNA can be isolated is tongue tissue, optionally taste bud tissues or individual taste cells.

Amplification techniques using primers can also be used to amplify and isolate GPCR-B4 from DNA or RNA. The degenerate primers encoding the following amino acid sequences can also be used to amplify a sequence of GPCR-B4: SEQ ID NOS:5-6 (see, e.g., Dieffenfach & Dveksler, *PCR Primer: A Laboratory Manual* (1995)). These primers can be used, e.g., to amplify either the full length sequence or a probe of one to several hundred nucleotides, which is then used to screen a mammalian library for full-length GPCR-B4.

Nucleic acids encoding GPCR-B4 can also be isolated from expression libraries using antibodies as probes. Such polyclonal or monoclonal antibodies can be raised using the sequence of SEQ ID NOS:1-2 and 7.

GPCR-B4 polymorphic variants, alleles, and interspecies homologs that are substantially identical to GPCR-B4 can be isolated using GPCR-B4 nucleic acid probes, and oligonucleotides under stringent hybridization conditions, by screening libraries. Alternatively, expression libraries can be used to clone GPCR-B4 and GPCR-B4 polymorphic variants, alleles, and interspecies homologs, by detecting expressed homologs immunologically with antisera or purified antibodies made against GPCR-B4, which also recognize and selectively bind to the GPCR-B4 homolog.

To make a cDNA library, one should choose a source that is rich in GPCR-B4 mRNA, e.g., tongue tissue, or isolated taste buds. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25:263-269 (1983); Sambrook et al., supra; Ausubel et al., supra).

For a genomic library, the DNA is extracted from the tissue and either mechanically sheared or enzymatically digested to yield fragments of about 12-20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180-182 (1977). Colony hybridization is carried out as generally described in Grunstein et al., *Proc. Natl. Acad. Sci, USA.,* 72:3961-3965 (1975).

An alternative method of isolating GPCR-B4 nucleic acid and its homologs combines the use of synthetic oligonucleotide primers and amplification of an RNA or PNA template (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of GPCR-B4 directly from mRNA, from cDNA, from genomic libraries or cDNA libraries. Degenerate oligonucleotides can be designed to amplify GPCR-B4 homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of GPCR-B4 encoding mRNA in physiological samples, for nucleic acid sequencing, or for other purposes. Genes amplified by the PCR reaction can be purified from agarose gels and cloned into an appropriate vector.

Gene expression of GPCR-B4 can also be analyzed by techniques known in the art, e.g., reverse transcription and amplification of mRNA, isolation of total RNA or poly $A^+$ RNA, northern blotting, dot blotting, in situ hybridization, RNase protection, probing DNA microchip arrays, and the like. In one embodiment, high density oligonucleotide analysis technology (e.g., GeneChip™) is used to identify homologs and polymorphic variants of the GFCRs of the invention. In the case where the homologs being identified are linked to a known disease, they can be used with. GeneChip™ as a diagnostic tool in detecting the disease in a biological sample, see, e.g., Gunthand et al., *AIDS Res. Hum. Retroviruses* 14: 869-876 (1998); Kozal et al., *Nat. Med.* 2:753-759 (1996); Matson et al., *Anal. Biochem.* 224:110-106 (1995); Lockhart et al., *Nat. Biotechnol.* 14:1675-1680 (1996); Gingeras et al., *Genome Res.* 8:435448 (1998); Hacia et al., *Nucleic Acids Res.* 26:3865-3866 (1998).

Synthetic oligonucleotides can be used to construct recombinant GPCR-B4 genes for use as probes or for expression of protein. This method is performed using a series of overlapping oligonucleotides usually 40-120 bp in length, representing both the sense and nonsense strands of the gene. These DNA fragments are then annealed, ligated and cloned. Alternatively, amplification techniques can be used with precise primers to amplify a specific subsequence of the GPCR-B4 nucleic acid. The specific subsequence is then ligated into an expression vector.

The nucleic acid encoding GPCR-B4 is typically cloned into intermediate vectors before transformation into prokaryotic or eukaryotic cells for replication and/or expression. These intermediate vectors are typically prokaryote vectors, e.g., plasmids, or shuttle vectors.

Optionally, nucleic acids encoding chimeric proteins comprising GPCR-B4 or domains thereof can be made according to standard techniques. For example, a domain such as ligand binding domain, an extracellular domain, a transmembrane domain (e.g., one comprising seven transmembrane regions and corresponding extracellular and cytosolic loops), the transmembrane domain and a cytoplasmic domain, an active site, a subunit association region, etc., can be covalently linked to a heterologous protein. For example, an extracellular domain can be linked to a heterologous GPCR transmembrane domain, or a heterologous GPCR extracellular domain can be linked to a transmembrane domain. Other heterologous proteins of choice include, e.g., green fluorescent protein, β-gal, glutamate receptor, and the rhodopsin presequence.

C. Expression in Prokaryotes and Eukaryotes

To obtain high level expression of a cloned gene or nucleic acid, such as those cDNAs encoding GPCR-B4, one typically subclones GPCR-B4 into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. Bacterial expression systems for expressing the GPCR-B4 protein are available in, e.g., *E. coli, Bacillus* sp., and *Salmonella* (Palva et al., *Gene* 22:229-235 (1983); Mosbach et al., *Nature* 302:543-545 (1983). Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the GPCR-B4 encoding nucleic acid in host cells. A typical expression cassette thus contains a promoter operably linked to the nucleic acid sequence encoding GPCR-B4 and signals required for efficient polyadenylation of the transcript, ribosome binding sites, and translation termination. The nucleic acid sequence encoding GPCR-B4 may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as using a baculovirus vector in insect cells, with a GPCR-B4 encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen Such that they do not interfere with the replication of the DNA in eukaryotic cells, if necessary.

Standard transfection methods are used to produce bacterial, mammalian, yeast or insect cell lines that express large quantities of GPCR-B4 protein, which are then purified using standard techniques (see, e.g., Colley et al., *J. Biol. Chem.* 264:17619-17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing GPCR-B4.

After the expression vector is introduced into the cells, the transfected cells are cultured under conditions favoring expression of GPCR-B4, which is recovered from the culture using standard techniques identified below.

IV. Purification of GPCR-B4

Either naturally occurring or recombinant GPCR-B4 can be purified for use in functional assays. Optionally, recombinant GPCR-B4 is purified. Naturally occurring GPCR-B4 is purified, e.g., from mammalian tissue such as tongue tissue, and any other source of a GPCR-B4 homolog. Recombinant GPCR-B4 is purified from any suitable bacterial or eukaryotic expression system, e.g., CHO cells or insect cells.

GPCR-B4 may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant GPCR-B4 is being purified. For example, proteins having established molecular adhesion properties can be reversible fused to GPCR-B4. With the appropriate ligand, GPCR-B4 can be selectively adsorbed to a purification column and then freed from the column in a relatively pure form. The fused protein is then removed by enzymatic activity. Finally GPCR-B4 could be purified using immunoaffinity columns.

A. Purification of GPCR-B4 from Recombinant Cells

Recombinant proteins are expressed by transformed bacteria or eukaryotic cells such as CHO cells or insect cells in large amounts, typically after promoter induction; but expression can be constitutive. Promoter induction with IPTG is a one example of an inducible promoter system. Cells are grown according to standard procedures in the art. Fresh or frozen cells are used for isolation of protein.

Proteins expressed in bacteria may form insoluble aggregates ("inclusion bodies"). Several protocols are suitable for purification of GPCR-B4 inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM MgCl$_2$, 1 mM DTT, 0.1 mM ATP, and 1 mM PMSF. The cell suspension can be lysed using 2-3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. GFCR-B4 is separated from other bacterial proteins by standard separation techniques, e.g., with Ni-NTA agarose resin.

Alternatively, it is possible to purify GPCR-B4 from bacteria periplasm. After lysis of the bacteria, when GPCR-B4 is exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying GPCR-B4

Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of GPCR-B4 can be used to isolated it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

GPCR-B4 can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

V. Immunological Detection of GPCR-B4

In addition to the detection of GPCR-B4 genes and gene expression using nucleic acid hybridization technology, one can also use immunoassays to detect GRCR-B4, e.g., to identify taste receptor cells and variants of GPCR-B4. Immunoassays can be used to qualitatively or quantitatively analyze GPCR-B4. A general overview of the applicable technology can be found in Harlow & Lane, *Antibodies: A Laboratory Manual* (1988).

A. Antibodies to GPCR-B4

Methods of producing polyclonal and monoclonal antibodies that react specifically with GPCR-B4 are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495-497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)).

A number of GPCR-B4 comprising immunogens may be used to produce antibodies specifically reactive with GPCR-B4. For example, recombinant GPCR-B4 or an antigenic fragment thereof, is isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to GPCR-B4. When appropriately high titers of antibody to the immunogen are obtained, blood is collected from the animal and antisera are prepared. Further fractionation of the antisera to enrich for antibodies reactive to the protein can be done if desired (see Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, *Eur. J. Immunol.* 6:511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246:1275-1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-GPCR-B4 proteins or even other related proteins from other organisms, using a competitive binding immunoassay. Specific polyclonal antisera and monoclonal antibodies will usually bind with a $K_d$ of at least about 0.1 mM, more usually at least about 1 µM, optionally at least about 0.1 µM or better, and optionally 0.01 µM or better.

Once GPCR-B4 specific antibodies are available, GPCR-B4 can be detected by a variety of immunoassay methods. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in *Enzyme Immunoassay* (Maggio, ed., 1980); and Harlow & Lane, supra.

B. Immunological Binding Assays

GPCR-B4 can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case the GPCR-B4 or antigenic subsequence thereof). The antibody (e.g., anti-GPCR-B4) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled GPCR-B4 polypeptide or a labeled anti-GPCR-B4 antibody. Alternatively, the labeling agent may be a third moiety, such a secondary antibody, that specifically binds to the antibody/GPCR-B4 complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.* 111:1401-1406 (1973); Akerstrom et al. *J. Immunol.* 135: 2589-2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non-competitive Assay Formats

Immunoassays for detecting GPCR-B4 in samples may be either competitive or noncompetitive. Noncompetitive immunoassays are assays in which the amount of antigen is directly measured. In one preferred "sandwich" assay, for example, the anti-GPCR-B4 antibodies can be bound directly to a solid substrate on which they are immobilized. These immobilized antibodies then capture GPCR-B4 present in the test sample. GPCR-B4 is thus immobilized is then bound by a labeling agent, such as a second GPCR-B4 antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of GPCR-B4 present in the sample is measured indirectly by measuring the amount of a known, added (exogenous) GPCR-B4 displaced (competed away) from an anti-GPCR-134 antibody by the unknown GPCR-B4 present in a sample. In one competitive assay, a known amount of GPCR-B4 is added to a sample and the sample is then contacted with an antibody that specifically binds to GPCR-B4. The amount of exogenous GPCR-B4 bound to the antibody is inversely proportional to the concentration of GPCR-B4 present in the sample. In a particularly preferred embodiment, the antibody is immobilized on a solid substrate. The amount of GPCR-B4 bound to the antibody may be determined either by measuring the amount of GPCR-B4 present in a GPCR-B4/antibody complex, or alternatively by measuring the amount of remaining uncomplexed protein. The amount of GPCR-134 may be detected by providing a labeled GPCR-B4 molecule.

A hapten inhibition assay is another preferred competitive assay. In this assay the known GPCR-B4, is immobilized on a solid substrate. A known amount of anti-GPCR-B4 antibody is added to the sample, and the sample is then contacted with the immobilized GPCR-B4. The amount of anti-GPCR-B4 antibody bound to the known immobilized GPCR-B4 is inversely proportional to the amount of GPCR-B4 present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-Reactivity Determinations

Immunoassays in the competitive binding format can also be used for crossreactivity determinations. For example, a protein at least partially encoded by SEQ ID NOS:1-2, and 7 can be immobilized to a solid support. Proteins (e.g., GPCR-B4 proteins and homologs) are added to the assay that compete for binding of the antisera to the immobilized antigen. The ability of the added proteins to compete for binding of the antisera to the immobilized protein is compared to the ability of GPCR-B4 encoded by SEQ ID NO:1-2, or 7 to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs.

The immunoabsorbed and pooled antisera are then used in a competitive binding immunoassay as described above to compare a second protein, thought to be perhaps an allele or polymorphic variant of GPCR-B4, to the immunogen protein (i.e., GPCR-B4 of SEQ ID NOS:1-2 or 7). In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by SEQ ID NOS:1-2, or 7 that is required to inhibit 50% of binding, then the second protein is said to specifically bind to the polyclonal antibodies generated to a GPCR-84 immunogen.

Other Assay Formats

Western blot (immunoblot) analysis is used to detect and quantify the presence of GPCR-B4 in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind GPCR-B4. The anti-GPCR-B4 antibodies specifically bind to the GPCR-B4 on the solid support. These antibodies may be directly labeled or alternatively may be subsequently detected using labeled antibodies (e.g., labeled sheep anti-mouse antibodies) that specifically bind to the anti-GPCR-B4 antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34-41 (1986)).

Reduction of Non-Specific Binding.

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition, in particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize GPCR-B4, or secondary antibodies that recognize anti-GPCR-B4.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

VI. Assays for Modulators of GPCR-B4

A. Assays for GPCR-B4 Activity

GPCR-B4 and its alleles and polymorphic variants are G-protein coupled receptors that participate in taste transduction. The activity of GPCR-B4 polypeptides can be assessed using a variety of in vitro and in vivo assays to determine functional, chemical, and physical effects, e.g., measuring ligand binding (e.g., radioactive ligand binding), second messengers (e.g., cAMP, cGMP, $IP_3$, DAG, or $Ca^{2+}$), ion flux, phosphorylation levels, transcription levels, neurotransmitter levels, and the like. Furthermore, such assays can be used to test for inhibitors and activators of GPCR-B4. Modulators can also be genetically altered versions of GPCR-B4. Such modulators of taste transduction activity are useful for customizing taste.

The GPCR-B4 of the assay will be selected from a polypeptide having a sequence of SEQ ID NOS:1-2, or 7 or conservatively modified variant thereof. Alternatively, the GPCR-B4 of the assay will be derived from a eukaryote and include an amino acid subsequence having amino acid sequence identity SEQ ID NOS:1-2, or 7. Generally, the amino acid sequence identity will be at least 70%, optionally at least 85%, optionally at least 90-95%. Optionally, the polypeptide of the assays will comprise a domain of GPCR-B4, such as an extracellular domain, transmembrane domain, cytoplasmic domain, ligand binding domain, subunit association domain, active site, and the like. Either GPCR-B4 or a domain thereof can be covalently linked to a heterologous protein to create a chimeric protein used in the assays described herein.

Modulators of GPCR-134 activity are tested using GPCR-B4 polypeptides as described above, either recombinant or naturally occurring. The protein can be isolated, expressed in a cell, expressed in a membrane derived from a cell, expressed in tissue or in an animal, either recombinant or naturally occurring. For example, tongue slices, dissociated cells from a tongue, transformed cells, or membranes can be used. Modulation is tested using one of the in vitro or in vivo assays described herein. Taste transduction can also be examined in vitro with soluble or solid state reactions, using a chimeric molecule such as an extracellular domain of a receptor covalently linked to a heterologous signal transduction domain, or a heterologous extracellular domain covalently linked to the transmembrane and or cytoplasmic domain of a receptor. Furthermore, ligand-binding domains of the protein of interest can be used in vitro in soluble or solid state reactions to assay for ligand binding.

Ligand binding to GPCR-B4, a domain, or chimeric protein can be tested in solution, in a bilayer membrane, attached to a solid phase, in a lipid monolayer, or in vesicles. Binding of a modulator can be tested using, e.g., changes in spectroscopic characteristics (e.g., fluorescence, absorbance, refractive index) hydrodynamic (e.g., shape), chromatographic, or solubility properties.

Receptor-G-protein interactions can also be examined. For example, binding of the G-protein to the receptor or its release from the receptor can be examined. For example, in the absence of GTP, an activator will lead to the formation of a tight complex of a G protein (all three subunits) with the receptor. This complex can be detected in a variety of ways, as noted above. Such an assay can be modified to search for inhibitors. Add an activator to the receptor and G protein in the absence of GTP, form a tight complex, and then screen for inhibitors by looking at dissociation of the receptor-G protein complex. In the presence of GTP, release of the alpha subunit of the G protein from the other two G protein subunits serves as a criterion of activation.

An activated or inhibited G-protein will in turn alter the properties of target enzymes, channels, and other effector proteins. The classic examples are the activation of cGMP phosphodiesterase by transducin in the visual system, adenylate cyclase by the stimulatory G-protein, phospholipase C by Gq and other cognate G proteins, and modulation of diverse channels by Gi and other G proteins. Downstream consequences can also be examined such as generation of diacyl glycerol and IP3 by phospholipase C, and in turn, for calcium mobilization by IP3.

Activated GPCR receptors become substrates for kinases that phosphorylate the C-terminal tail of the receptor (and possibly other sites as well). Thus, activators will promote the transfer of $^{32}P$ from gamma-labeled GTP to the receptor, which can be assayed with a scintillation counter. The phosphorylation of the C-terminal tail will promote the binding of arrestin-like proteins and will interfere with the binding of G-proteins. The kinase/arrestin pathway plays a key role in the desensitization of many GPCR receptors. For example, compounds that modulate the duration a taste receptor stays active would be useful as a means of prolonging a desired taste or cutting off an unpleasant one. For a general review of GPCR signal transduction and methods of assaying signal transduction, see, e.g., *Methods in Enzymology*, vols. 237 and 238 (1994) and volume 96 (1983); Bourne et al., *Nature* 10:349:117-27 (1991); Bourne et al., *Nature* 348:125-32 (1990); Pitcher et al., *Annu. Rev. Biochem.* 67:653-92 (1998).

Samples or assays that are treated with a potential GPCR-B4 inhibitor or activator are compared to control samples without the test compound, to examine the extent of modulation. Control samples (untreated with activators or inhibitors) are assigned a relative GPCR-B4 activity value of 100. Inhibition of GPCR-B4 is achieved when the GPCR-B4 activity value relative to the control is about 90%, optionally 50%, optionally 25-0%. Activation of GPCR-B4 is achieved when the GPCR-B4 activity value relative to the control is 110%, optionally 150%, 200-500%, or 1000-2000%.

Changes in ion flux may be assessed by determining changes in polarization (i.e., electrical potential) of the cell or membrane expressing GPCR-B4. One means to determine changes in cellular polarization is by measuring changes in current (thereby measuring changes in polarization) with voltage-clamp and patch-clamp techniques, e.g., the "cell-attached" mode, the "inside-out" mode, and the "whole cell" mode (see, e.g., Ackerman et al., *New Engl. J. Med.* 336: 1575-1595 (1997)). Whole cell currents are conveniently determined using the standard methodology (see, e.g., Hamil et al., *PFlugers. Archiv.* 391:85 (1981). Other known assays include: radiolabeled ion flux assays and fluorescence assays using voltage-sensitive dyes (see, e.g., Vestergarrd-Bogind ex al., *J. Membrane Biol.* 88:67-75 (1988); Gonzales & Tsien, *Chem. Biol.* 4:269-277 (1997); Daniel et al., *J. Pharmacol. Meth.* 25:185-193 (1991); Holevinsky et al., *J. Membrane Biology* 137:59-70 (1994)). Generally, the compounds to be tested are present in the range from 1 pM to 100 mM.

The effects of the test compounds upon the function of the polypeptides can be measured by examining any of the parameters described above. Any suitable physiological change that affects GPCR activity can be used to assess the influence of a test compound on the polypeptides of this invention. When the functional consequences are determined using intact cells or animals, one can also measure a variety of effects such as transmitter release, hormone release, transcriptional changes to both known and uncharacterized genetic markers (e.g., northern blots), changes in cell metabolism such as cell growth or pH changes, and changes in intracellular second messengers such as $Ca^{2+}$, IP3 or cAMP.

Preferred assays for G-protein coupled receptors include cells that are loaded with ion or voltage sensitive dyes to report receptor activity. Assays for determining activity of such receptors can also use known agonists and antagonists for other G-protein coupled receptors as negative or positive controls to assess activity of tested compounds. In assays for identifying modulatory compounds (e.g., agonists, antagonists), changes in the level of ions in the cytoplasm or membrane voltage will be monitored using an ion sensitive or membrane voltage fluorescent indicator, respectively. Among the ion-sensitive indicators and voltage probes that may be employed are those disclosed in the Molecular Probes 1997 Catalog. For G-protein coupled receptors, promiscuous G-proteins such as $G\alpha15$ and $G\alpha16$ can be used in the assay of choice (Wilkie et al., *Proc. Nat'l Acad. Sci. USA* 88:10049-10053 (1991)). Such promiscuous G-proteins allow coupling of a wide range of receptors.

Receptor activation typically initiates subsequent intracellular events, e.g., increases in second messengers such as IP3, which releases intracellular stores of calcium ions. Activation of some G-protein coupled receptors stimulates the formation of inositol triphosphate (IP3) through phospholipase C-mediated hydrolysis of phosphatidylinositol (Benidge & Irvine, *Nature* 312:315-21 (1984)). IP3 in turn stimulates the release of intracellular calcium ion stores. Thus, a change in cytoplasmic calcium ion levels, or a change in second messenger levels such as IP3 can be used to assess G-protein coupled receptor function. Cells expressing such G-protein coupled receptors may exhibit increased cytoplasmic calcium levels as a result of contribution from both intracellular stores and via activation of ion channels, in which case it may be desirable although not necessary to conduct such assays in calcium-free buffer, optionally supplemented with a chelating agent such as EGTA, to distinguish fluorescence response resulting from calcium release from internal stores.

Other assays can involve determining the activity of receptors which, when activated, result in a change in the level of intracellular cyclic nucleotides, e.g., cAMP or cGMP, by activating or inhibiting enzymes such as adenylate cyclase. There are cyclic nucleotide-gated ion channels, e.g., rod photoreceptor cell channels and olfactory neuron channels that are permeable to cations upon activation by binding of cAMP or cGMP (see, e.g., Altenhofen et al., *Proc. Natl. Acad. Sci. U.S.A.* 88:9868-9872 (1991) and Dhallan et al., *Nature* 347: 184-187 (1990)). In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay. Cells for this type of assay can be made by co-transfection of a host cell with DNA encoding a cyclic nucleotide-crated ion channel, GPCR phosphatase and DNA encoding a receptor (e.g., certain glutamate receptors, muscarinic acetylcholine receptors, dopamine receptors, serotonin receptors, and the like), which, when activated, causes a change in cyclic nucleotide levels in the cytoplasm.

In a preferred embodiment, GPCR-B4 activity is measured by expressing GPCR-B4 in a heterologous cell with a promiscuous G-protein that links the receptor to a phospholipase C signal transduction pathway (see Offermanns & Simon, *J. Biol. Chem.* 270:15175-15180 (1995); see also Example II). Optionally the cell line is HEK-293 (which does not naturally express GPCR-B4) and the promiscuous G-protein is Gα15 (Offermanns & Simon, supra). Modulation of taste transduction is assayed by measuring changes in intracellular $Ca^{2+}$ levels, which change in response to modulation of the GPCR-B4 signal transduction pathway via administration of a molecule that associates with GPCR-B4. Changes in $Ca^{2+}$ levels are optionally measured using fluorescent $Ca^{2+}$ indicator dyes and fluorometric imaging.

In one embodiment, the changes in intracellular cAMP or cGMP can be measured using immunoassays. The method described in Offermanns & Simon, *J. Biol. Chem.* 270:15175-15180 (1995) may be used to determine the level of cAMP. Also, the method described in Felley-Bosco et al., *Am. J. Resp. Cell and Mol. Biol.* 11:159-164 (1994) may be used to determine the level of cGMP. Further, an assay kit for measuring cAMP and/or cGMP is described in U.S. Pat. No. 4,115,538, herein incorporated by reference.

In another embodiment, phosphatidyl inositol (PI) hydrolysis can be analyzed according to U.S. Pat. No. 5,436, 128, herein incorporated by reference. Briefly, the assay involves labeling of cells with $^3H$-myoinositol for 48 or more hrs. The labeled cells are treated with a test compound for one hour. The treated cells are lysed and extracted in chloroform-methanol-water after which the inositol phosphates were separated by ion exchange chromatography and quantified by scintillation counting. Fold stimulation is determined by calculating the ratio of cpm in the presence of agonist to cpm in the presence of buffer control. Likewise, fold inhibition is determined by calculating the ratio of cpm in the presence of antagonist to cpm in the presence of buffer control (which may or may not contain an agonist).

In another embodiment, transcription levels can be measured to assess the effects of a test compound on signal transduction. A host cell containing the protein of interest is contacted with a test compound for a sufficient time to effect any interactions, and then the level of gene expression is measured. The amount of time to effect such interactions may be empirically determined, such as by running a time course and measuring the level of transcription as a function of time. The amount of transcription may be measured by using any method known to those of skill in the art to be suitable. For example, mRNA expression of the protein of interest may be detected using northern blots or their polypeptide products may be identified using immunoassays. Alternatively, transcription based assays using reporter gene may be used as described in U.S. Pat. No. 5,436,128, herein incorporated by reference. The reporter genes can be, e.g., chloramphenicol acetyltransferase, firefly luciferase, bacterial luciferase, β-galactosidase and alkaline phosphatase. Furthermore, the protein of interest can be used as an indirect reporter via attachment to a second reporter such as green fluorescent protein (see, e.g., Mistili & Spector, *Nature Biotechnology* 15:961-964 (1997)).

The amount of transcription is then compared to the amount of transcription in either the same cell in the absence of the test compound, or it may be compared with the amount of transcription in a substantially identical cell that lacks the protein of interest. A substantially identical cell may be derived from the same cells from which the recombinant cell was prepared but which had not been modified by introduction of heterologous DNA. Any difference in the amount of transcription indicates that the test compound has in some manner altered the activity of the protein of interest.

B. Modulators

The compounds tested as modulators of GPCR-B4 can be any small chemical compound, or a biological entity, such as a protein, sugar, nucleic acid or lipid. Alternatively, modulators can be genetically altered versions of GPCR-B4. Typically, test compounds will be small chemical molecules and peptides. Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g. U.S. Pat. No. 5,010,175, Furka, *J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-0.6913 (1993)), vinylogous polypeptides (Hagihara et al., *J. Amer. Chem. Soc.* 114:6568 (1992)), non-peptidal peptidomimetics with glucose scaffolding (Hirschmann et al., *J. Amer. Chem. Soc,* 114:9217-9218 (1992)), analogous organic syntheses of small compound libraries (Chen et al. *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309-314 (1996) and PCT/US96/10287), carbohydrate libraries (see, e.g., Liang et al., *Science,* 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

C. Solid State and Soluble High Throughput Assays

In one embodiment the invention provide soluble assays using molecules such as a domain such as ligand binding domain, an extracellular domain, a transmembrane domain (e.g., one comprising seven transmembrane regions and cytosolic loops), the transmembrane domain and a cytoplasmic domain, an active site, a subunit association region, etc.; a domain that is covalently linked to a heterologous protein to create a chimeric molecule; GPCR-B4; or a cell or tissue expressing GPCR-B4, either naturally occurring or recombinant. In another embodiment, the invention provides solid phase based in vitro assays in a high throughput format, where the domain, chimeric molecule, GPCR-B4, or cell or tissue expressing GPCR-B4 is attached to a solid phase substrate.

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100-about 1500 different compounds. It is possible to assay several different plates per day; assay screens for up to about 6,000-20,000 different compounds is possible using the integrated systems of the invention. More recently, microfluidic approaches to reagent manipulation have been developed, e.g., by Caliper Technologies (Palo Alto, Calif.).

The molecule of interest can be bound to the solid state component, directly or indirectly, via covalent or non covalent linkage e.g., via a tag. The tag can be any of a variety of components. In general, a molecule which binds the tag (a tag binder) is fixed to a solid support, and the tagged molecule of interest (e.g., the taste transduction molecule of interest) is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.)

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, *The Adhesion Molecule Faces Book I* (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Sac.* 85:2149-2154 (1963) (describing solid phase synthesis of, e.g., peptides); Geysen et al. *J. Immun. Meth.* 102:259-274 (1987) (describing synthesis of solid phase components on pins); Frank & Doring, *Tetrahedron* 44:60316040 (1988) (describing synthesis of various peptide sequences on cellulose disks); Fodor et al., *Science,* 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

D. Computer-Based Assays

Yet another assay for compounds that modulate GPCR-B4 activity involves computer assisted drug design, in which a computer system is used to generate a three-dimensional structure of GPCR-B4 based on the structural information encoded by the amino acid sequence. The input amino acid sequence interacts directly and actively with a preestablished algorithm in a computer program to yield secondary, tertiary, and quaternary structural models of the protein. The models of the protein structure are then examined to identify regions of the structure that have the ability to bind, e.g., ligands. These regions are then used to identify ligands that bind to the protein.

The three-dimensional structural model of the protein is generated by entering protein amino acid sequences of at least 10 amino acid residues or corresponding nucleic acid sequences encoding a GPCR-B4 polypeptide into the computer system. The amino acid sequence of the polypeptide of the nucleic acid encoding the polypeptide is selected from the group consisting of SEQ ID NOS:1-2, or 7 or SEQ ID NOS: 3-4, or 8 and conservatively modified versions thereof. The amino acid sequence represents the primary sequence or subsequence of the protein, which encodes the structural information of the protein. At least 10 residues of the amino acid sequence (or a nucleotide sequence encoding 10 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by interne sites, and by RAM. The three-dimensional structural model of the protein is then generated by the interaction of the amino acid sequence and the computer system, using software known to those of skill in the art.

The amino acid sequence represents a primary structure that encodes the information necessary to form the secondary, tertiary and quaternary structure of the protein of interest. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential ligand binding regions are identified by the computer system. Three-dimensional structures for potential ligands are generated by entering amino acid or nucleotide sequences or chemical formulas of compounds, as described above. The three-dimensional structure of the potential ligand is then compared to that of the GPCR-B4 protein to identify ligands that bind to GPCR-B4. Binding affinity between the protein and ligands is determined using energy terms to determine which ligands have an enhanced probability of binding to the protein.

Computer systems are also used to screen for mutations, polymorphic variants, alleles and interspecies homologs of GPCR-B4 genes. Such mutations can be associated with disease states or genetic traits. As described above, GerteChip™ and related technology can also be used to screen for mutations, polymorphic variants, alleles and interspecies homologs. Once the variants are identified, diagnostic assays can be used to identify patients having such mutated genes. Identification of the mutated GPCR-B4 genes involves receiving input of a first nucleic acid or amino acid sequence encoding GPCR-B4, selected from the group consisting of SEQ ID NOS:1-2, and 7, or SEQ ID NOS:3-4, and 8 and conservatively modified versions thereof. The sequence is entered into the computer system as described above. The first nucleic acid or amino acid sequence is then compared to a second nucleic acid or amino acid sequence that has substantial identity to the first sequence. The second sequence is entered into the computer system in the manner described above. Once the first and second sequences are compared, nucleotide or amino acid differences between the sequences are identified. Such sequences can represent allelic differences in GPCR-B4 genes, and mutations associated with disease states and genetic traits.

VIII. Kits

GPCR-B4 and its homologs are a useful tool for identifying taste receptor cells, for forensics and paternity determinations, and for examining taste transduction. GPCR-B4 specific reagents that specifically hybridize to GPCR-B4 nucleic acid, such as GPCR-B4 probes and primers, and GPCR-B4 specific reagents that specifically bind to the GPCR-B4 protein, e.g., GPCR-B4 antibodies are used to examine taste cell expression and taste transduction regulation.

Nucleic acid assays for the presence of GPCR-B4 DNA and RNA in a sample include numerous techniques are known to those skilled in the art, such as Southern analysis, northern analysis, dot blots, RNase protection, S1 analysis, amplification techniques such as PCR and LCR, and in situ hybridization. In in situ hybridization, for example, the target nucleic acid is liberated from its cellular surroundings in such as to be available for hybridization within the cell while preserving the cellular morphology for subsequent interpretation and analysis (see Example I). The following articles provide an overview of the art of in situ hybridization: Singer et al., *Biotechniques* 4:230-250 (1986); Haase et al., *Methods in Virology*, vol. VII, pp. 189-226 (1984); and *Nucleic Acid Hybridization: A Practical Approach* (Hames et al., eds. 1987). In addition, GPCR-B4 protein can be detected with the various immunoassay techniques described above. The test sample is typically compared to both a positive control (e.g., a sample expressing recombinant GPCR-B4) and a negative control.

The present invention also provides for kits for screening for modulators of GPCR-B4. Such kits can be prepared from readily available materials and reagents. For example, such kits can comprise any one or more of the following materials: GPCR-B4, reaction tubes, and instructions for testing GPCR-B4 activity. Optionally, the kit contains biologically active GPCR-B4. A wide variety of kits and components can be prepared according to the present invention, depending upon the intended user of the kit and the particular needs of the user.

IX. Administration and Pharmaceutical Compositions

Taste modulators can be administered directly to the mammalian subject for modulation of taste in vivo. Administration is by any of the routes normally used for introducing a modulator compound into ultimate contact with the tissue to be treated, optionally the tongue or mouth. The taste modulators are administered in any suitable manner, optionally with pharmaceutically acceptable carriers. Suitable methods of administering such modulators are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington's Pharmaceutical Sciences*, 17$^{th}$ ed. 1985)).

The taste modulators, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, by orally, topically, intravenously, intraperitoreally, intravesically or intrathecally. Optionally, the compositions are administered orally or nasally. The formulations of compounds can be presented in unit-dose or multi-dose sealed containers, such as ampules and vials. Solutions and suspensions can be prepared from sterile powders, granules, and tablets of the kind previously described. The modulators can also be administered as part a of prepared food or drug.

The dose administered to a patient, in the context of the present invention should be sufficient to effect a beneficial response in the subject over time. The dose will be determined by the efficacy of the particular taste modulators employed and the condition of the subject, as well as the body weight or surface area of the area to be treated. The size of the dose also will be determined by the existence, nature, and extent of any adverse side-effects that accompany the administration of a particular compound or vector in a particular subject.

In determining the effective amount of the modulator to be administered in a physician may evaluate circulating plasma levels of the modulator, modulator toxicities, and the production of anti-modulator antibodies. In general, the dose equivalent of a modulator is from about 1 ng/kg to 10 mg/kg for a typical subject.

For administration, taste modulators of the present invention can be administered at a rate determined by the LD-50 of the modulator, and the side-effects of the inhibitor at various concentrations, as applied to the mass and overall health of the subject. Administration can be accomplished via single or divided doses.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill in the art will readily recognize a variety of noncritical parameters that could be changed or modified to yield essentially similar results.

Example I

Cloning and Expression of GPCR-B4 cDNA libraries made from rat circumvallate and fungiform single cells was used isolate the GPCR nucleic acids of the invention.

Single foliate and fungiform papillae were isolated from the rat tongue (10 papillae each) and first strand cDNA was prepared from each papillae using single cell library construction methods (see, e.g., Bernhardt et al., *J. Physiol.* 490: 325-336 (1996); Dulac & Axel, *Cell* 83:195-206 (1995)). 20 different cDNA populations were assayed for those positive for a taste receptor marker (TCP #1, also known as clone 27-59; see patent application attorney docket no. 02307E-084200, filed Jul. 28, 1998) to ensure that the cDNA was from taste receptor cells. The cDNAs were also screened with GPCR-B3, a G-protein coupled receptor clone (see U.S. Ser. No. 60/094,465, filed Jul. 28, 1998). Three positive papillae were identified and used as a source of cDNA for PCR amplifications using degenerate primers designed to encode motifs highly conserved amongst VR/mGluR/CaST/GPCR-B3 receptors. Preferred primers came from the area between transmembrane domains 6 and 7: [Y/N]FNEAK (SEQ ID NO:9) and PKCY[I/V]I (SEQ ID NO:10). Degenerate PCR products were subcloned into a Bluescript vector as HindIII fragments, and 52 PCR products were sequences. Twenty of these products corresponded to GPCR-B3. 8 of the products encoded a novel GPCR-B4 sequence.

Mouse interspecies homologs of GPCR-134 were isolated using the rat GPCR-B4 clones as probes for genomic and cDNA libraries. The nucleotide and amino acid sequences of GPCR-B4 are provided, respectively, in SEQ ID NO:1-2, and 7 and SEQ ID NO:3-4, and 8.

Taste cell specific expression of GPCR-B4 is confirmed using the clones as probes for in situ hybridization to tongue tissue sections. All clones demonstrate specific or preferential expression in taste buds.

Example II

GPCR is a Taste Transduction Receptor

The distinctive topographic distribution of GPCR-B4 and the behavioral representation of bitter transduction suggest a correlation between the sites of expression of B4 (circumvallate papillae, but not fungiform or geschmackstreifen) and bitter sensitivity. To determine the ligand selectivity of GPCR-B4, expression in heterologous cells was used. One issue for GPCR expression in heterologous cells is determining how to couple the GPCR to a G-protein and an appropriate signaling pathway, in this example, the G-protein subunit Gα15 was used, which promiscuously couples a wide range of GPCRs to the phospholipase Gα15 mediated signaling pathway (Offermans & Simon, *J. Biol. Chem.* 270:15175-15180 (1995)). Consequently, receptor activity can be effectively measured by recording ligand-induced changes in $[Ca^{2+}]_i$ using fluorescent $Ca^{2+}$-indicator dyes and fluorometric imaging.

To insure expression of GPCR-B4 in the plasma membrane, a variety of cell lines and expression vectors were tested. As a control for these studies, the cells were transfected with a mammalian γ-opiod receptor; this receptor does not normally couple to PLC, so all agonist-induced changes in $[Ca^{2+}]_i$ reflect coupling through Gα15. An HEK-293 line expressing SV40 T-antigen was co-transfected with a TK-Gα15, CMV-γ-opiod and a pEAK-10 episomal vector (Edge Biosystems) containing a EF1a-[B4-GPCR] construct. Transfection efficiencies were determined using CMV-GFP constructs. Control cells expressing γ-opiod/Gα15 respond robustly to DAMGO (a γ-opiod agonist), but do not respond to sweet or bitter tastants, or unrelated agonists (data not shown). These responses are dependent on Gα15, and have the appropriate temporal resolution, with rapid onset following application of the stimulus. Notably, cells expressing B4/Gα15 or B4/Gα15/γ-opiod respond to the well characterized bitter tastant phenylthiocarbamide (PTC), but not to any of a number of natural or artificial sweeteners. This activity is entirely B4 receptor dependent, and occurs at physiologically relevant concentrations of PTC (300 μM-5 mM).

These results suggest GPCR-B4 is involved in bitter taste transduction, and provide an experimentally tractable system for future experiments, including studies of tastant specificity and selectivity, the definition of the native bitter signaling pathway, and perhaps understanding the molecular basis of human psychophysical studies demonstrating dramatic differences in PTC tasting between "tasters" and "non-tasters."

SEQUENCE LISTING

```
Rat GPCR-B4 amino acid sequence--SEQ ID NO: 1
MGPQARTLCLLSLLLHVLPKPGKLVENSDFHLAGDYLLGGLFTLHANVKSISHLSYLQVP
KCNEFTMKVLGYNLMQAMRFAVEEINNCSSLLPGVLLGYEMVDVCYLSNNIHPGLYFLAQ
DDDLLPILKDYSQYMPHVVAVIGPDNSESAITVSNILSHFLIPQITYSAISDKLRDKRHF
PSMLRTVPSATHHIEAMVQLMVHFQWNWIVVLVSDDDYGRENSHLLSQRLTKTSDICIAF
QEVLPIPESSQVMRSEEQRQLDNILDKLRRTSARVVVVFSPELSLYSFFHEVLRWNFTGF
VWIASESWAIDPVLHNLTELRHTGTFLGVTIQPGFSQFRVRRDKPGYPVPNTTNLR
TTCNQDCDACLNTTKSFNNILILSGERVVYSVYSAVYAVAHALHRLLGCNRVRCTKQKVY
PWQLLREIWHVNFTLLGNRLFFDQQGDMPMLLDIIQWQWDLSQNPFQSIASYSPTSKRLT
YINNVSWYTPNNTVPVSMCSKSCQPGQMKKSVGLHPCCFECLDCMPGTYLNRSADEFNCL
SCPGSMWSYKNDITCFQRRPTFLEWHEVPTIVVAILAALGFFSTLAILFIFWRHFQTPMV
RSAGGPMCFLMLVPLLLAFGMVPVYVGPPTVFSCFCRQAFFTVCFSICLSCITVRSFQIV
CVFKMARRLPSAYSFWMRYHGPYVFVAFITAIKVALVVGNMLATTINPIGRTDPDDPNIM
ILSCHPNYRNGLLFNTSMDLLLSVLGFSFAYMGKELPTNYNEAKFITLSMTFSFTSSISL
CTFMSVHDGVLVTIMDLLVTVLNFLAIGLGYFGPKCYMILFYPERNTSAYFNSMIQGYTM
RKS Mouse GPCR-B4 amino acid sequence--SEQ ID NO: 2
MGPQARTLHLLFLLLHALPKPVMLVGNSDFHLAGDYLLGGLFTLHANVKSVSHLSYLQVP
KCNEYNMKVLGYNLMQAMRFAVEEINNCSSLLPGVLLGYEMVDVCYLSNNIQPGLYFLSQ
IDDFLPILKDYSQYRPQVVAVIGPDNSESAITVSNILSYFLVPQVTYSAITDKLQDKRRF
PAMLRTVPSATHHIEAMVQLMVHFQWNWIVVLVSDDDYGRENSHLLSQRLTNTGDICIAF
QEVLPVPEPNQAVRPEEQDQLDNILDKLRRTSARVVVIFSPELSLHNFFREVLRWNFTGF
VWIASESWAIDPVLHNLTELRHTGTFLGVTIQRVSIPGFSQFRVRHDKPGYRMPNETSLR
TTCNQDCDACMNITESFNNVLMLSGERVVYSVYSAVYAVAHTLHRLLHCNQVRCTKQIVY
PWQLLREIWHVNFTLLGNQLFFDEQGDMPMLLDIIQWQWGLSQNPFQSIASYSPTETRLT
YISNVSWYTPNNTVPISMCSKSCQPGQMKKPIGLHPCCFECVDCPPDTYLNRSVDEFNCL
SCPGSMWSYKNNIACFKRRLAFLEWHEVPTIVVTILAALGFISTLAILLIFWRHFQTPMV
RSAGGPMCFLMLVPLLLAFGMVPVYVGPPTVFSCFCRQAFFTVCFSVCLSCITVRSFQIV
CVFKMARRLPSAYGFWMRYHGPYVFVAFITAVKVALVAGNMLATTINPIGRTDPDDPNII
ILSCHPNYRNGLLFNTSMDLLLSVLGFSFAYVGKELPTNYNEAKFITLSMTFSFTSSISL
CTFMSVHDGVLVTIMDLLVTVLNFLAIGLGYFGPKCYMILFYPERNTSAYFNSMIQGYTM
RKS Rat GPCR-34 nucleotide sequence--SEQ ID NO: 3
CACTTTGCTGTCATGGGTCCCCAGGCAAGGACACTCTGCTTGCTGTCTCTCCTGCTGCAT
GTTCTGCCTAAGCCAGGCAAGCTGGTAGAGAACTCTGACTTCCACCTGGCCGGGGACTAC
CTCCTGGGTGGCCTCTTTACCCTCCATGCCAACGTGAAGAGCATCTCCCACCTCAGCTAC
CTGCAGGTGCCCAAGTGCAATGAGTTCACCATGAAGGTGTTGGGCTACAACCTCATGCAG
GCCATGCGTTTCGCTGTGGAGGAGATCAACAACTGTAGCTCCCTGCTACCCGGCGTGCTG
CTCGGCTACGAGATGGTGGATGTCTGTTACCTCTCCAACAATATCCACCCTGGGCTCTAC
```

SEQUENCE LISTING-continued

```
TTCCTGGCACAGGACGACGACCTCCTGCCCATCCTCAAAGACTACAGCCAGTACATGCCC
CACGTGGTGGCTGTCATTGGCCCCGACAACTCTGAGTCCGCCATTACCGTGTCCAACATT
CTCTCTCATTTCCTCATCCCACAGATCACATACAGCGCCATCTCCGACAAGCTGCGGGAC
AAGCGGCACTTCCCTAGCATGCTACGCACAGTGCCGAGCGCCACCCACCACATCGAGGCC
ATGGTGCAGCTGATGGTTCACTTCCAATGGAACTGGATTGTGGTGCTGGTGAGCGACGAC
GATTACGGCCGCGAGAACAGCCACCTGTTGAGCCAGCGTCTGACCAAAACGAGCGACATC
TGCATTGCCTTCCAGGAGGTTCTGCCCATACCTGAGTCCAGCCAGGTCATGAGGTCCGAG
GAGCAGAGACAACTGGACAACATCCTGGACAAGCTGCGGCGGACCTCGGCGCGCGTCGTG
GTGGTGTTCTCGCCCGAGCTGAGCCTGTATAGCTTCTTTCACGAGGTGCTCCGCTGGAAC
TTCACGGGTTTTGTGTGGATCGCCTCTGAGTCCTGGGCTATCGACCCAGTTCTGCATAAC
CTCACGGAGCTGCGCCACACGGGTACTTTTCTGGGCGTCACCATCCAGAGGGTGTCCATC
CCTGGCTTCAGTCAGTTCCGAGTGCGCCGTGACAAGCCAGGGTATCCCGTGCCTAACACG
ACCAACCTGCGGACGACCTGCAACCAGGACTGTGACGCCTGCTTGAACACCACCAAGTCC
TTCAACAACATCCTTATACTTTCGGGGGAGCGCGTGGTCTACAGCGTGTACTCGGCAGTT
TACGCGGTGGCCCATGCCCTCCACAGACTCCTCGGCTGTAACCGGGTCCGCTGCACCAAG
CAAAAGGTCTACCCGTGGCAGCTACTCAGGGAGATCTGGCACGTCAACTTCACGCTCCTG
GGTAACCGGCTCTTCTTTGACCAACAAGGGGACATGCCGATGCTCTTGGACATCATCCAG
TGGCAGTGGGACCTGAGCCAGAATCCCTTCCAAAGCATCGCCTCCTATTCTCCCACCAGC
AAGAGGCTAACCTACATTAACAATGTGTCCTGGTACACCCCCAACAACACGGTCCCTGTC
TCCATGTGTTCCAAGAGCTGCCAGCCAGGGCAAATGAAAAAGTCTGTGGGCCTCCACCCT
TGTTGCTTCGAGTGCTTGGATTGTATGCCAGGCACCTACCTCAACCGCTCAGCAGATGAG
TTTAACTGTCTGTCCTGCCCGGGTTCCATGTGGTCCTACAAGAACGACATCACTTGCTTC
CAGCGGCGGCCTACCTTCCTGGAGTGGCACGAAGTGCCCACCATCGTGGTGGCCATACTG
GCTGCCCTGGGCTTCTTCAGTACACTGGCCATTCTTTTCATCTTCTGGAGACATTTCCAG
ACACCCATGGTGCGCTCGGCCGGTGGCCCCATGTGCTTCCTGATGCTCGTGCCCCTGCTG
CTGGCGTTTGGGATGGTGCCCGTGTATGGGGCCCCCCACGGTCTTCTCATGCTTCTGC
CGACAGGCTTTCTTCACCGTCTGCTTCTCCATCTGCCTATCCTGCATCACCGTGCGCTCC
TTCCAGATCGTGTGTGTCTTCAAGATGGCCAGACGCCTGCCAAGTGCCTACAGTTTTTGG
ATGCGTTACCACGGGCCCTATGTCTTCGTGGCCTTCATCACGGCCATCAAGGTGGCCCTG
GTGGTGGGCAACATGCTGGCCACCACCATCAACCCCATTGGCCGGACCGACCCGGATGAC
CCCAACATCATGATCCTCTCGTGCCACCCTAACTACCGCAACGGGCTACTGTTCAACACC
AGCATGGACTTGCTGCTGTCTGTGCTGGGTTTCAGCTTCGCTTACATGGGCAAGGAGCTG
CCCACCAACTACAACGAAGCCAAGTTCATCACTCTCAGCATGACCTTCTCCTTCACCTCC
TCCATCTCCCTCTGCACCTTCATGTCTGTGCACGACGGCGTGCTGGTCACCATCATGGAC
CTCCTGGTCACTGTGCTCAACTTCCTGGCCATCGGCTTGGGATACTTTGGCCCCAAGTGT
TACATGATCCTTTTCTACCCGGAGCGCAACACCTCAGCCTATTTCAATAGCATGATCCAG
GGCTACACCATGAGGAAGAGCTAGCTCCGCCCACCGGCCTCAGCAGCAGAGCCCCCGGCC
ACGTTAATGGTGTTCCTCTGCCATTCTCTGCAGCGTAGCTATTTTTACCCACATAGCGCT
TAAAATACCCATGATGCACTCTCCCCGACCCCCAAGCCATTTCACTGGCCAGGACCTAC
CACCCACTTATAGATGAAACCACCAAGGCGCCCTATGGGGCTCCAAGGATGCCTACCAC
TGCCATCTGGTGGTCACAGTGAGCACATGCGGGCCGTGCCCATGGCTCCCAGCCAGCTG
GTGGCTAGTGGCTGTGAGGCCAGATGTCTGTGTATCTGAGTTCCTGGGAAGCAGAGACTG
GGGCTCCTGTGTTCTAATGGTCAGATGGGCATCATGGGCCCTTCATTATTGCTTACGAAT
AAACTTCCCTCCGGTGAAAAAAAAAAAAAAAAAAAAAAAAAAAAAAAAAAAAAA
```

Mouse GPCR-B4 nucleotide sequence--SEQ ID NO: 4
```
ATGGGACCCCAGGCGAGGACACTCCATTTGCTGTTTCTCCTGCTGCATGCTCTGCCTAAG
CCAGTCATGCTGGTAGGGAACTCCGACTTTCACCTGGCTGGGGACTACCTCCTGGGTGGC
CTCTTTACCCTCCATGCCAACGTGAAGAGTGTCTCTCACCTCAGCTACCTGCAGGTGCCC
AAGTGCAATGAGTACAACATGAAGGTGTTGGGCTACAACCTCATGCCAGGCCATGCGATTC
GCCGTGGAGGAAATCAACAACTGTAGCTCTTTGCTGCCCGGCGTGCTGCTCGGCTACGAG
ATGGTGGATGTCTGCTACCTCTCCAACAATATCCAGCCTGGGCTCTACTTCCTGTCACAG
ATAGATGACTTCCTGCCCATCCTCAAAGACTACAGCCAGTACAGGCCCCAAGTGGTGGCT
GTTATTGGCCCAGCACAACTCTGAGTCTGCCATCACCGTGTCCAACATTCTCTCCTACTTC
CTCGTGCCACAGGTCACATATAGCGCCATCACCGACAAGCTGCAAGACAAGCGGCGCTTC
CCTGCCATGCTGCGCACTGTGCCCAGCGCCACCCACCACATCGAGGCCATGGTGCAACTG
ATGGTTCACTTCCAGTGGAACTGGATCGTGGTGCTGGTGAGCGATGACGATTATGGCCGA
GAGAACAGCCACCTGCTGAGCCAGCGTCTGACCAACACTGGCGACATCTGCATTGCCTTC
CAGGAGGTTCTGCCCGTACCAGAACCCAACCAGGCTGTGAGGCCTGAGGAGCAGGACCAA
CTGGACAACATCCTGGACAAGCTGCGGCGACTTCGGCGCGTGTGGTGGTGATATTCTCG
CCCGGAGCTGAGCCTGCACAACTTCTTCCGTGAGGTGCTGCGCTGGAACTTCACGGGCTTT
GTGTGGATTGCCTCTGAGTCCTGGGCCATCGACCCTGTTCTACACAACCTCACAGAGCTG
CGCCACACGGGCACTTTCCTGGGTGTCACCATCCAGAGGGTGTCCATCCCTGGCTTCAGC
CAGTTCCGAGTGCGCCATGACAAGCCAGGGTATCGCATGCCTAACGAGACCAGCCTGCGG
ACTACCTGTAACCAGGACTGCGACGCCTGCATGAACATCACTGAGTCCTTCAACAACGTT
CTCATGCTTTCGGGGGAGCGTGTGGTCTACAGCGTGTACTCGGCCGTCTACGCGGTGGCC
CACACCCTCCACAGACTCCTCACTGCAATCAGGTCCGCTGCCAAGCAAATCGTCTAT
CCATGGCAGCTACTCAGGGAGATCTGGCATGTCAACTTCACGCTCCTGGGCAACCAGCTC
TTCTTCGACGAACAAGGGGACATGCCGATGCTCCTGGACATCATCCAGTGGCAGTGGGGC
CTGAGCCAGAACCCCTTCCAAAGCATCGCCTCCTACTCCCCCACCGAGACGAGGCTGACC
TACATTAGCAATGTGTCCTGGTACACCCCCAACAACACGGTCCCATATCCATGTGTTCT
AAGAGTTGCCAGCCTGGGCAAATGAAAAAACCCATAGGCCTCCACCCATGCTGCTTCGAG
TGTGTGGACTGTCCGCCGGACACCTACCTCAACCGATCAGTAGATGAGTTTAACTGTCTG
TCCTGCCCGGGTTCCATGTGGTCTTACAAGAACAACATCGCTTGCTTCAAGCGGCGGCTG
GCCTTCCTGGAGTGGCACGAAGTGCCCACTATCGTGGTGGCCATCCTGGGCGCCCTGGGC
TTCATCAGTACGCTGGCCATTCTGCTCATCTTCTGGAGACATTTCCAGACGCCCATGGTG
CGCTCGGCGGGCGGCCCCATGTGCTTCCTGATGCTGGTGCCCCTGCTGCTGGCGTTCGGG
ATGGTCCCCGTGTATGGGGCCCCCCACGGTCTTCTCCTGTTTCTGCCGCCAGGCTTTC
TTCACCGTTTGCTTCTCCGTCTGCCTCTCCTGCATCACGGTGCGCTCCTTCCAGATTGTG
TGCGTCTTCAAGATGGCCAGACGCCTGCCAAGCGCCTACGGTTTCTGGATGCGTTACCAC
```

SEQUENCE LISTING-continued

```
GGGCCCTACGTCTTCGTGGCCTTCATCACGGCCGTCAAGGTGGCCCTGGTGGCGGGCAAC
ATGCTGGCCACCACCATCAACCCCATTGGCCGGACCGACCCCGATGACCCCAATATCATA
ATCCTCTCCTGCCACCCTAACTACCGCAACGGGCTACTCTTCAACACCAGCATGGACTTG
CTGCTGTCCGTGCTGGGTTTCAGCTTCGCGTACGTGGGCAAGGAACTGCCCACCAACTAC
AACGAAGCCAAGTTCATCACCCTCAGCATGACCTTCTCCTTCACCTCCTCCATCTCCCTC
TGCACGTTCATGTCTGTCCACGATGGCGTGCTGGTCACCATCATGGATCTCCTGGTCACT
GTGCTCAACTTTCTGGCCATCGGCTTGGGGTACTTTGGCCCCAAATGTTACATGATCCTT
TTCTACCCGGAGCGCAACACTTCAGCTTATTTCAATAGCATGATTCAGGGCTACACGATG
AGGAAGAGCTAG
```

Human GPCR-B4 amino acid sequence--SEQ ID NO: 7
```
ITYSAISDELRDKVRFPALLRTTPSADHHVEAMVQLMLHFRWNWIIVLVSSDTYGRDNGQ
LLGERVARRDICIAFQETLPTLQPNQNMTSEERQRLVTIVDKLQQSTARVVVVFSPDLTL
YHFFNEVLRQNFTGAVWIASESWAIDPVLHNLTELGHLGTFLGITIQSVPIPGFSEFREW
GPQAGPPPLSRTSQSYTCNQECDNCLNATLSFNTILRLSGERVVYSVYSAVYAVAHALHS
LLGCDKSTCTKRVVYPWQLLEEIWKVNFTLLDHQIFFDPQGDVALHLEIVQWQWDRSQNP
FQSVASYYPLQRQLKNIKTSLHTVNNTIPSMSCSKRCQSGQKKKPVGIHVCCFECIDCLP
GTFLNHTECPNNEWSYQSETSCFKRQLVFLEWHEAPTIAVALLAALGFLSTLAILVIFWR
HFQTPIVRSAGGPMCFLMLTLLLVAYMVVPVYVGPPKVSTCLCRQALFPLCFTICISCIA
VRSFQIVCAFKMASRFPRAYSYWVRYQGPYVSMAFITVLKMVIVVIGMLARPQSHPRTDP
DDPKITIVSCNPNYRNSLLFNTSLDLLLSVVGFSFAYMGKELPTNYNEAKFITLSMTFYF
TSSVSLCTFMSAYSGVLVTIVDLLVTVLNLLAISLGYFGPKCYMILFYPERNTPAYFNSM
IQGYTMRRD
```

Human GPCR-B4 nucleotide sequence--SEQ ID NO: 8
```
ATCACCTACAGCGCCATCAGCGATGAGCTGCGAGACAAGGTGCGCTTCCCGGCTTTGCTG
CGTACCACACCCAGCGCCGACCACCACGTCGAGGCCATGGTGCAGCTGATGCTGCACTTC
CGCTGGAACTGGATCATTGTGCTGGTGAGCAGCGACACCTATGGCCGCGACAATGGCCAG
CTGCTTGGCGAGCGCGTGGCCCGGCGCGACATCTGCATCGCCTTCCAGGAGACGCTGCCC
ACACTGCAGCCCAACCAGAACATGACGTCAGAGGAGCGCCAGCGCCTGGTGACCATTGTG
GACAAGCTGCAGCAGAGCACAGCGCGTCGTGGTCGTGTTCTCGCCCGACCTGACCCTG
TACCACTTCTTCAATGAGGTGCTGCGCCAGAACTTCACGGGCGCCGTGTGGATCGCCTCC
GAGTCCTGGGCCATCGACCCGGTCCTGCACAACCTCACGGAGCTGGGCCACTTGGGCACT
TTCCTGGGCATCACCATCCAGAGCGTGCCCATCCCGGGCTTCAGTGAGTTCCGCGAGTGG
GGCCCACAGGCTGGGCCGCCACCCCTCAGCAGGACCAGCCAGAGCTATACCTGCAACCAG
GAGTGCGACAACTGCCTGAACGCCACCTTGTCCTTCAACACCATTCTCAGGCTCTCTGGG
GAGCGTGTCGTCTACAGCGTGTACTCTGCGGTCTATGCTGTGGCCCATGCCCTGCACAGC
CTCCTCGGCTGTGACAAAAGCACCTGCACCAAGAGGGTGGTCTACGCCTGGCAGCTGCTT
GAGGAGATCTGGAAGGTCAACTTCACTCTCCTGGACCACCAAATCTTCTTCGACCCGCAA
GGGGACGTGGCTCTGCACTTGGAGATTGTCCAGTGGCAATGGGACCGGAGCCAGAATCCC
TTCCAGAGCGTCGCCTCCTACTACCCCTGCAGCGACAGCTGAAGAACATCAAGACATCT
CTGCACACCGTCAACAACACGATCCCTATGTCCATGTGTTCCAAGAGGTGCCAGTCAGGG
CAAAAGAAGAAGCCTGTGGGCATCCACGTCTGCTGCTTCGAGTGCATCGACTGCCTTCCC
GGCACCTTCCTCAACCACACTGAATGCCCGAATAACGAGTGGTCCTACCAGAGTGAGACC
TCCTGCTTCAAGCGGCAGCTGGTCTTCCTGGAATGGCATGAGGCACCCACCATCGCTGTG
GCCCTGCTGGCCGCCCTGGGCTTCCTCAGCACCCTGGCCATCCTGGTGATATTCTGGAGG
CACTTCCAGACACCCATAGTTCGCTCGGCTGGGGGcCCCATGTGCTTCCTGATGCTGACA
CTGCTGCTGGTGGCATACATGGTGGTCCCGGTGTACGTGGGGCCGCCCAAGGTCTCCACC
TGCCTCTGCCGCCAGGCCCTCTTTCCCCTCTGCTTCACAATTTGCATCTCCTGTATCGCC
GTGCGTTCTTTCCAGATCGTCTGCGCCTTCAAGATGGCCAGCCGCTTCCCACGCGCCTAC
AGCTACTGGGTCCGCTACCAGGGGCCCTACGTCTCTATGGCATTTATCACGGTACTCAAA
ATGGTCATTGTGGTAATTGGCATGCTGGCACGGCCTCAGTCCCACCCCGTACTGACCCC
GATGACCCCAAGATCACAATTGTCTCCTGTAACCCCAACTACCGCAACAGCCTGCTGTTC
AACACCAGCCTGGACCTGCTGCTCTCAGTGGTGGGTTTCAGCTTCGCCTACATGGGCAAA
GAGCTGCCCACCAACTACAACGAGGCCAAGTTCATCACCCTCAGCATGACCTTCTATTTC
ACCTCATCCGTCTCCCTCTGCACCTTCATGTCTGCCTACAGCGGGGTGCTGGTCACCATC
GTGGACCTCTTGGTCACTGTGCTCAACCTCCTGGCCATCAGCCTGGGCTACTTCGGCCCC
AAGTGCTACATGATCCTCTTCTACCCGGAGCGCAACACGCCCGCCTACTTCAACAGCATG
ATCCAGGGCTACACCATGAGGAGGGACTAG
```

What is claimed is:

1. A method for identifying a compound that modulates sensory signaling in sensory cells, the method comprising the steps of:
   (i) contacting the compound with a polypeptide comprising an extracellular domain of a sensory transduction G-protein coupled receptor, the extracellular domain comprising greater than about 90% amino acid sequence identity to the extracellular domain of SEQ ID NO:1 or SEQ ID NO:2; and
   (ii) determining the functional effect of the compound upon the extracellular domain.

2. The method of claim 1, wherein the extracellular domain is linked to a solid phase.

3. The method of claim 1, wherein the functional effect is a chemical effect.

4. The method of claim 1, wherein the functional effect is determined by measuring binding of the compound to the extracellular domain.

5. The method of claim 1, wherein the polypeptide is recombinant.

6. The method of claim 1, Wherein the polypeptide is from a rat, a mouse, or a human.

7. The method of claim 1, wherein the polypeptide is expressed in a cell or cell membrane, 8. The method of claim 1, wherein the functional effect is a physical effect.

9. The method of claim 1, wherein the extracellular domain of the contacted polypeptide comprises greater than about 90% amino acid sequence identity to the extracellular domain of SEQ ID NO:1.

10. The method of claim 1, wherein the extracellular domain of the contacted polypeptide comprises greater than about 95% amino acid sequence identity to the extracellular domain of SEQ ID NO:1.

11. The method of claim 1, wherein the extracellular domain of the contacted polypeptide comprises greater than about 90% amino acid sequence identity to the extracellular domain of SEQ ID NO:2.

12. The method of claim 1, wherein the extracellular domain of the contacted polypeptide comprises greater than about 95% amino acid sequence identity to the extracellular domain of SEQ ID NO:2.

* * * * *

SEQUENCE LISTING

<160> NUMBER OF SEQ ID NOS: 10

<210> SEQ ID NO 1
<211> LENGTH: 843
<212> TYPE: PRT
<213> ORGANISM: Rattus sp.
<220> FEATURE:
<223> OTHER INFORMATION: rat G-protein coupled receptor (GPCR) B4 amino acid sequence

<400> SEQUENCE: 1

```
Met Gly Pro Gln Ala Arg Thr Leu Cys Leu Leu Ser Leu Leu Leu His
  1               5                  10                  15
Val Leu Pro Lys Pro Gly Lys Leu Val Glu Asn Ser Asp Phe His Leu
             20                  25                  30
Ala Gly Asp Tyr Leu Leu Gly Leu Phe Thr Leu His Ala Asn Val
             35                  40                  45
Lys Ser Ile Ser His Leu Ser Tyr Leu Gln Val Pro Lys Cys Asn Glu
         50                  55                  60
Phe Thr Met Lys Val Leu Gly Tyr Asn Leu Met Gln Ala Met Arg Phe
 65                  70                  75                  80
Ala Val Glu Glu Ile Asn Asn Cys Ser Ser Leu Leu Pro Gly Val Leu
                 85                  90                  95
Leu Gly Tyr Glu Met Val Asp Val Cys Tyr Leu Ser Asn Asn Ile His
            100                 105                 110
Pro Gly Leu Tyr Phe Leu Ala Gln Asp Asp Leu Leu Pro Ile Leu
            115                 120                 125
Lys Asp Tyr Ser Gln Tyr Met Pro His Val Val Ala Val Ile Gly Pro
    130                 135                 140
Asp Asn Ser Glu Ser Ala Ile Thr Val Ser Asn Ile Leu Ser His Phe
145                 150                 155                 160
Leu Ile Pro Gln Ile Thr Tyr Ser Ala Ile Ser Asp Lys Leu Arg Asp
                165                 170                 175
Lys Arg His Phe Pro Ser Met Leu Arg Thr Val Pro Ser Ala Thr His
                180                 185                 190
His Ile Glu Ala Met Val Gln Leu Met Val His Phe Gln Trp Asn Trp
            195                 200                 205
Ile Val Val Leu Val Ser Asp Asp Tyr Gly Arg Glu Asn Ser His
    210                 215                 220
Leu Leu Ser Gln Arg Leu Thr Lys Thr Ser Asp Ile Cys Ile Ala Phe
225                 230                 235                 240
Gln Glu Val Leu Pro Ile Pro Glu Ser Ser Gln Val Met Arg Ser Glu
                245                 250                 255
Glu Gln Arg Gln Leu Asp Asn Ile Leu Asp Lys Leu Arg Thr Ser
            260                 265                 270
Ala Arg Val Val Val Phe Ser Pro Glu Leu Ser Leu Tyr Ser Phe
    275                 280                 285
Phe His Glu Val Leu Arg Trp Asn Phe Thr Gly Phe Val Trp Ile Ala
290                 295                 300
Ser Glu Ser Trp Ala Ile Asp Pro Val Leu His Asn Leu Thr Glu Leu
305                 310                 315                 320
Arg His Thr Gly Thr Phe Leu Gly Val Thr Ile Gln Arg Val Ser Ile
                325                 330                 335
Pro Gly Phe Ser Gln Phe Arg Val Arg Arg Asp Lys Pro Gly Tyr Pro
                340                 345                 350
Val Pro Asn Thr Thr Asn Leu Arg Thr Thr Cys Asn Gln Asp Cys Asp
            355                 360                 365
Ala Cys Leu Asn Thr Thr Lys Ser Phe Asn Asn Ile Leu Ile Leu Ser
    370                 375                 380
Gly Glu Arg Val Val Tyr Ser Val Tyr Ser Ala Val Tyr Ala Val Ala
385                 390                 395                 400
His Ala Leu His Arg Leu Leu Gly Cys Asn Arg Val Arg Cys Thr Lys
                405                 410                 415
Gln Lys Val Tyr Pro Trp Gln Leu Leu Arg Glu Ile Trp His Val Asn
            420                 425                 430
```

-continued

Phe Thr Leu Leu Gly Asn Arg Leu Phe Phe Asp Gln Gln Gly Asp Met
    435                 440                 445

Pro Met Leu Leu Asp Ile Ile Gln Trp Gln Trp Asp Leu Ser Gln Asn
450                 455                 460

Pro Phe Gln Ser Ile Ala Ser Tyr Ser Pro Thr Ser Lys Arg Leu Thr
465                 470                 475                 480

Tyr Ile Asn Asn Val Ser Trp Tyr Thr Pro Asn Asn Thr Val Pro Val
                485                 490                 495

Ser Met Cys Ser Lys Ser Cys Gln Pro Gly Gln Met Lys Lys Ser Val
            500                 505                 510

Gly Leu His Pro Cys Cys Phe Glu Cys Leu Asp Cys Met Pro Gly Thr
        515                 520                 525

Tyr Leu Asn Arg Ser Ala Asp Glu Phe Asn Cys Leu Ser Cys Pro Gly
    530                 535                 540

Ser Met Trp Ser Tyr Lys Asn Asp Ile Thr Cys Phe Gln Arg Arg Pro
545                 550                 555                 560

Thr Phe Leu Glu Trp His Glu Val Pro Thr Ile Val Val Ala Ile Leu
                565                 570                 575

Ala Ala Leu Gly Phe Phe Ser Thr Leu Ala Ile Leu Phe Ile Phe Trp
            580                 585                 590

Arg His Phe Gln Thr Pro Met Val Arg Ser Ala Gly Gly Pro Met Cys
        595                 600                 605

Phe Leu Met Leu Val Pro Leu Leu Leu Ala Phe Gly Met Val Pro Val
    610                 615                 620

Tyr Val Gly Pro Pro Thr Val Phe Ser Cys Phe Cys Arg Gln Ala Phe
625                 630                 635                 640

Phe Thr Val Cys Phe Ser Ile Cys Leu Ser Cys Ile Thr Val Arg Ser
                645                 650                 655

Phe Gln Ile Val Cys Val Phe Lys Met Ala Arg Arg Leu Pro Ser Ala
            660                 665                 670

Tyr Ser Phe Trp Met Arg Tyr His Gly Pro Tyr Val Phe Val Ala Phe
        675                 680                 685

Ile Thr Ala Ile Lys Val Ala Leu Val Val Gly Asn Met Leu Ala Thr
    690                 695                 700

Thr Ile Asn Pro Ile Gly Arg Thr Asp Pro Asp Pro Asn Ile Met
705                 710                 715                 720

Ile Leu Ser Cys His Pro Asn Tyr Arg Asn Gly Leu Leu Phe Asn Thr
                725                 730                 735

Ser Met Asp Leu Leu Ser Val Leu Gly Phe Ser Phe Ala Tyr Met
            740                 745                 750

Gly Lys Glu Leu Pro Thr Asn Tyr Asn Glu Ala Lys Phe Ile Thr Leu
        755                 760                 765

Ser Met Thr Phe Ser Phe Thr Ser Ser Ile Ser Leu Cys Thr Phe Met
    770                 775                 780

Ser Val His Asp Gly Val Leu Val Thr Ile Met Asp Leu Leu Val Thr
785                 790                 795                 800

Val Leu Asn Phe Leu Ala Ile Gly Leu Gly Tyr Phe Gly Pro Lys Cys
                805                 810                 815

Tyr Met Ile Leu Phe Tyr Pro Glu Arg Asn Thr Ser Ala Tyr Phe Asn
            820                 825                 830

Ser Met Ile Gln Gly Tyr Thr Met Arg Lys Ser
        835                 840

```
<210> SEQ ID NO 2
<211> LENGTH: 843
<212> TYPE: PRT
<213> ORGANISM: Mus sp.
<220> FEATURE:
<223> OTHER INFORMATION: mouse G-protein coupled receptor (GPCR) B4
      amino acid sequence

<400> SEQUENCE: 2
```

Met Gly Pro Gln Ala Arg Thr Leu His Leu Leu Phe Leu Leu His
 1               5                  10                  15

Ala Leu Pro Lys Pro Val Met Leu Val Gly Asn Ser Asp Phe His Leu
                20                  25                  30

Ala Gly Asp Tyr Leu Leu Gly Gly Leu Phe Thr Leu His Ala Asn Val
            35                  40                  45

Lys Ser Val Ser His Leu Ser Tyr Leu Gln Val Pro Lys Cys Asn Glu
        50                  55                  60

Tyr Asn Met Lys Val Leu Gly Tyr Asn Leu Met Gln Ala Met Arg Phe
 65                  70                  75                  80

Ala Val Glu Glu Ile Asn Asn Cys Ser Ser Leu Leu Pro Gly Val Leu
                85                  90                  95

Leu Gly Tyr Glu Met Val Asp Val Cys Tyr Leu Ser Asn Asn Ile Gln
            100                 105                 110

Pro Gly Leu Tyr Phe Leu Ser Gln Ile Asp Asp Phe Leu Pro Ile Leu
        115                 120                 125

Lys Asp Tyr Ser Gln Tyr Arg Pro Gln Val Val Ala Val Ile Gly Pro
    130                 135                 140

Asp Asn Ser Glu Ser Ala Ile Thr Val Ser Asn Ile Leu Ser Tyr Phe
145                 150                 155                 160

Leu Val Pro Gln Val Thr Tyr Ser Ala Ile Thr Asp Lys Leu Gln Asp
                165                 170                 175

Lys Arg Arg Phe Pro Ala Met Leu Arg Thr Val Pro Ser Ala Thr His
            180                 185                 190

His Ile Glu Ala Met Val Gln Leu Met Val His Phe Gln Trp Asn Trp
        195                 200                 205

Ile Val Val Leu Val Ser Asp Asp Tyr Gly Arg Glu Asn Ser His
    210                 215                 220

Leu Leu Ser Gln Arg Leu Thr Asn Thr Gly Asp Ile Cys Ile Ala Phe
225                 230                 235                 240

Gln Glu Val Leu Pro Val Pro Glu Pro Asn Gln Ala Val Arg Pro Glu
                245                 250                 255

Glu Gln Asp Gln Leu Asp Asn Ile Leu Asp Lys Leu Arg Arg Thr Ser
            260                 265                 270

Ala Arg Val Val Val Ile Phe Ser Pro Glu Leu Ser Leu His Asn Phe
        275                 280                 285

Phe Arg Glu Val Leu Arg Trp Asn Phe Thr Gly Phe Val Trp Ile Ala
    290                 295                 300

Ser Glu Ser Trp Ala Ile Asp Pro Val Leu His Asn Leu Thr Glu Leu
305                 310                 315                 320

Arg His Thr Gly Thr Phe Leu Gly Val Thr Ile Gln Arg Val Ser Ile
                325                 330                 335

Pro Gly Phe Ser Gln Phe Arg Val Arg His Asp Lys Pro Gly Tyr Arg
            340                 345                 350

Met Pro Asn Glu Thr Ser Leu Arg Thr Thr Cys Asn Gln Asp Cys Asp
        355                 360                 365

Ala Cys Met Asn Ile Thr Glu Ser Phe Asn Asn Val Leu Met Leu Ser

-continued

```
                    370                 375                 380
Gly Glu Arg Val Val Tyr Ser Val Tyr Ser Ala Val Tyr Ala Val Ala
385                 390                 395                 400

His Thr Leu His Arg Leu Leu His Cys Asn Gln Val Arg Cys Thr Lys
                    405                 410                 415

Gln Ile Val Tyr Pro Trp Gln Leu Leu Arg Glu Ile Trp His Val Asn
                    420                 425                 430

Phe Thr Leu Leu Gly Asn Gln Leu Phe Phe Asp Glu Gln Gly Asp Met
                    435                 440                 445

Pro Met Leu Leu Asp Ile Ile Gln Trp Gln Trp Gly Leu Ser Gln Asn
450                 455                 460

Pro Phe Gln Ser Ile Ala Ser Tyr Ser Pro Thr Glu Thr Arg Leu Thr
465                 470                 475                 480

Tyr Ile Ser Asn Val Ser Trp Tyr Thr Pro Asn Asn Thr Val Pro Ile
                    485                 490                 495

Ser Met Cys Ser Lys Ser Cys Gln Pro Gly Gln Met Lys Lys Pro Ile
                    500                 505                 510

Gly Leu His Pro Cys Cys Phe Glu Cys Val Asp Cys Pro Pro Asp Thr
                    515                 520                 525

Tyr Leu Asn Arg Ser Val Asp Glu Phe Asn Cys Leu Ser Cys Pro Gly
530                 535                 540

Ser Met Trp Ser Tyr Lys Asn Asn Ile Ala Cys Phe Lys Arg Arg Leu
545                 550                 555                 560

Ala Phe Leu Glu Trp His Glu Val Pro Thr Ile Val Thr Ile Leu
                    565                 570                 575

Ala Ala Leu Gly Phe Ile Ser Thr Leu Ala Ile Leu Ile Phe Trp
                    580                 585                 590

Arg His Phe Gln Thr Pro Met Val Arg Ser Ala Gly Gly Pro Met Cys
                    595                 600                 605

Phe Leu Met Leu Val Pro Leu Leu Ala Phe Gly Met Val Pro Val
610                 615                 620

Tyr Val Gly Pro Pro Thr Val Phe Ser Cys Phe Cys Arg Gln Ala Phe
625                 630                 635                 640

Phe Thr Val Cys Phe Ser Val Cys Leu Ser Cys Ile Thr Val Arg Ser
                    645                 650                 655

Phe Gln Ile Val Cys Val Phe Lys Met Ala Arg Arg Leu Pro Ser Ala
                    660                 665                 670

Tyr Gly Phe Trp Met Arg Tyr His Gly Pro Tyr Val Phe Val Ala Phe
                    675                 680                 685

Ile Thr Ala Val Lys Val Ala Leu Val Ala Gly Asn Met Leu Ala Thr
                    690                 695                 700

Thr Ile Asn Pro Ile Gly Arg Thr Asp Pro Asp Asp Pro Asn Ile Ile
705                 710                 715                 720

Ile Leu Ser Cys His Pro Asn Tyr Arg Asn Gly Leu Leu Phe Asn Thr
                    725                 730                 735

Ser Met Asp Leu Leu Ser Val Leu Gly Phe Ser Phe Ala Tyr Val
                    740                 745                 750

Gly Lys Glu Leu Pro Thr Asn Tyr Asn Glu Ala Lys Phe Ile Thr Leu
                    755                 760                 765

Ser Met Thr Phe Ser Phe Thr Ser Ser Ile Ser Leu Cys Thr Phe Met
                    770                 775                 780

Ser Val His Asp Gly Val Leu Val Thr Ile Met Asp Leu Leu Val Thr
785                 790                 795                 800
```

```
Val Leu Asn Phe Leu Ala Ile Gly Leu Gly Tyr Phe Gly Pro Lys Cys
            805                 810                 815

Tyr Met Ile Leu Phe Tyr Pro Glu Arg Asn Thr Ser Ala Tyr Phe Asn
            820                 825                 830

Ser Met Ile Gln Gly Tyr Thr Met Arg Lys Ser
            835                 840

<210> SEQ ID NO 3
<211> LENGTH: 2993
<212> TYPE: DNA
<213> ORGANISM: Rattus sp.
<220> FEATURE:
<223> OTHER INFORMATION: rat G-protein coupled receptor (GPCR) B4
      nucleotide sequence

<400> SEQUENCE: 3
cactttgctg tcatgggtcc ccaggcaagg acactctgct tgctgtctct cctgctgcat      60
gttctgccta agccaggcaa gctggtgaga actctgact tccacctggc cggggactac     120
ctcctgggtg gcctctttac cctccatgcc aacgtgaaga gcatctccca cctcagctac     180
ctgcaggtgc ccaagtgcaa tgagttcacc atgaaggtgt gggctacaa cctcatgcag     240 gccatgcgtt cgctgtgga ggagatcaac aactgtagct ccctgctacc cggcgtgctg     300
ctcggctacg agatggtgga tgtctgttac ctctccaaca atatccaccc tgggctctac     360
ttcctggcac aggacgacga cctcctgccc atcctcaaag actacagcca gtacatgccc     420
cacgtggtgg ctgtcattgg ccccgacaac tctgagtccg ccattaccgt gtccaacatt     480
ctctctcatt tcctcatccc acagatcaca tacagcgcca tctccgacaa gctgcgggac     540
aagcggcact tccctagcat gctacgcaca gtgcccagcg ccacccacca catcgaggcc     600
atggtgcagc tgatggttca cttccaatgg aactggattg tggtgctggt gagcgacgac     660
gattacggcc gcgagaacag ccacctgttg agccagcgtc tgaccaaaac gagcgacatc     720
tgcattgcct tccaggaggt tctgcccata cctgagtcca gccaggtcat gaggtccgag     780
gagcagagac aactggacaa catcctggac aagctgcggc ggacctcggc gcgcgtcgtg     840
gtggtgttct cgcccgagct gagcctgtat agcttctttc acgaggtgct ccgctggaac     900
ttcacgggtt ttgtgtggat cgcctctgag tcctgggcta tcgacccagt tctgcataac     960
ctcacggagc tgcgccacac gggtactttt ctgggcgtca ccatccagag ggtgtccatc     1020
cctggcttca gtcagttccg agtgcgccgt gacaagccag ggtatcccgt gcctaacacg     1080
accaacctgc ggacgacctg caaccaggac tgtgacgcct gcttgaacac caccaagtcc     1140
ttcaacaaca tccttatact ttcggggggag cgcgtggtct acagcgtgta ctcggcagtt     1200
tacgcggtgg cccatgccct ccacagactc ctcggctgta accgggtccg ctgcaccaag     1260
caaaaggtct acccgtggca gctactcagg gagatctggc acgtcaactt cacgctcctg     1320
ggtaaccggc tcttctttga ccaacaaggg gacatgccga tgctcttgga catcatccag     1380
tggcagtggg acctgagcca gaatcccttc aaagcatcg cctcctattc tcccaccagc     1440
aagaggctaa cctacattaa caatgtgtcc tggtacaccc caacaacac ggtccctgtc     1500 tccatgtgtt ccaagagctg ccagccaggg caaatgaaaa agtctgtggg cctccaccct     1560
tgttgcttcg agtgcttgga ttgtatgcca ggcacctacc tcaaccgctc agcagatgag     1620
tttaactgtc tgtcctgccc gggttccatg tggtcctaca agaacgacat cacttgcttc     1680
cagcggcggc ctaccttcct ggagtggcac gaagtgccca ccatcgtggt ggccatactg     1740
gctgccctgg gcttcttcag tacactggcc attcttttca tcttctggag acatttccag     1800
```

| | |
|---|---:|
| acacccatgg tgcgctcggc cggtggcccc atgtgcttcc tgatgctcgt gcccctgctg | 1860 |
| ctggcgtttg ggatggtgcc cgtgtatgtg gggcccccca cggtcttctc atgcttctgc | 1920 |
| cgacaggctt tcttcaccgt ctgcttctcc atctgcctat cctgcatcac cgtgcgctcc | 1980 |
| ttccagatcg tgtgtgtctt caagatggcc agacgcctgc caagtgccta cagttttggg | 2040 |
| atgcgttacc acgggcccta tgtcttcgtg gccttcatca cggccatcaa ggtggccctg | 2100 |
| gtggtgggca acatgctggc caccaccatc aaccccattg gccggaccga cccggatgac | 2160 |
| cccaacatca tgatcctctc gtgccaccct aactaccgca acgggctact gttcaacacc | 2220 |
| agcatggact gctgctgtc tgtgctgggt ttcagcttcg cttacatggg caaggagctg | 2280 |
| cccaccaact acaacgaagc caagttcatc actctcagca tgaccttctc cttcacctcc | 2340 |
| tccatctccc tctgcacctt catgtctgtg cacgacggcg tgctggtcac catcatggac | 2400 |
| ctcctggtca ctgtgctcaa cttcctggcc atcggcttgg atactttgg ccccaagtgt | 2460 |
| tacatgatcc ttttctaccc ggagcgcaac acctcagcct atttcaatag catgatccag | 2520 |
| ggctacacca tgaggaagag ctagctccgc ccaccggcct cagcagcaga gccccggcc | 2580 |
| acgttaatgg tgttcctctg ccattctctg cagcgtagct attttttaccc acatagcgct | 2640 |
| taaaataccc atgatgcact ctcccccgac ccccaagcca tttcactggc caggacctac | 2700 |
| cacccactta tagatgaaac caccaaggcg ccctatgggg ctccaaggat ggcctaccac | 2760 |
| tgccatctgg tggtcacagt gagcacatgc gggccgtggc ccatggctcc cagccagctg | 2820 |
| gtggctagtg gctgtgaggc cagatgtctg tgtatctgag ttcctgggaa gcagagactg | 2880 |
| gggctcctgt gttctaatgg tcagatgggc atcatgggcc cttcattatt gcttacgaat | 2940 |
| aaacttccct ccggtgaaaa aaaaaaaaaa aaaaaaaaaa aaaaaaaaaa aaa | 2993 |

<210> SEQ ID NO 4
<211> LENGTH: 2532
<212> TYPE: DNA
<213> ORGANISM: Mus sp.
<220> FEATURE:
<223> OTHER INFORMATION: mouse G-protein coupled receptor (GPCR) B4
      nucleotide sequence

<400> SEQUENCE: 4

| | |
|---|---:|
| atgggacccc aggcgaggac actccatttg ctgtttctcc tgctgcatgc tctgcctaag | 60 |
| ccagtcatgc tggtagggaa ctccgacttt cacctggctg gggactacct cctgggtggc | 120 |
| ctctttaccc tccatgccaa cgtgaagagt gtctctcacc tcagctacct gcaggtgccc | 180 |
| aagtgcaatg agtacaacat gaaggtgttg ggctacaacc tcatgcaggc catgcgattc | 240 |
| gccgtggagg aaatcaacaa ctgtagctct ttgctgcccg gcgtgctgct cggctacgag | 300 |
| atggtggatg tctgctacct ctccaacaat atccagcctg ggctctactt cctgtcacag | 360 |
| atagatgact ccctgcccat cctcaaagac tacagccagt acaggcccca agtggtggct | 420 |
| gttattggcc cagacaactc tgagtctgcc atcaccgtgt ccaacattct ctcctacttc | 480 |
| ctcgtgccac aggtcacata tagcgccatc accgacaagc tgcaagacaa gcggcgcttc | 540 |
| cctgccatgc tgcgcactgt gcccagcgcc acccaccaca tcgaggccat ggtgcaactg | 600 |
| atggttcact tccagtggaa ctggatcgtg tgctggtga gcgatgacga ttatggccga | 660 |
| gagaacagcc acctgctgag ccagcgtctg accaacactg cgacatctg cattgccttc | 720 |
| caggaggttc tgcccgtacc agaacccaac caggctgtga ggcctgagga gcaggaccaa | 780 |
| ctggacaaca tcctggacaa gctgcggcgg acttcggcgc gtgtggtggt gatattctcg | 840 |
| ccggagctga gcctgcacaa cttcttccgt gaggtgctgc gctggaactt cacgggcttt | 900 |

```
gtgtggattg cctctgagtc ctgggccatc gaccctgttc tacacaacct cacagagctg      960
cgccacacgg gcactttcct gggtgtcacc atccagaggg tgtccatccc tggcttcagc     1020
cagttccgag tgcgccatga caagccaggg tatcgcatgc taacgagac cagcctgcgg      1080 actacctgta accaggactg cgacgcctgc atgaacatca ctgagtcctt caacaacgtt     1140
ctcatgcttt cggggagcg tgtggtctac agcgtgtact cggccgtcta cgcggtggcc     1200
cacaccctcc acagactcct ccactgcaat caggtccgct gcaccaagca aatcgtctat     1260
ccatggcagc tactcaggga gatctggcat gtcaacttca cgctcctggg caaccagctc     1320
ttcttcgacg aacaagggga catgccgatg ctcctggaca tcatccagtg gcagtggggc     1380
ctgagccaga ccccttcca aagcatcgcc tcctactccc ccaccgagac gaggctgacc      1440
tacattagca atgtgtcctg gtacaccccc aacaacacgg tccccatatc catgtgttct     1500
aagagttgcc agcctgggca aatgaaaaaa cccataggcc tccacccatg ctgcttcgag     1560
tgtgtggact gtccgccgga cacctacctc aaccgatcag tagatgagtt taactgtctg     1620
tcctgcccgg gttccatgtg gtcttacaag aacaacatcg cttgcttcaa gcggcggctg     1680
gccttcctgg agtggcacga agtgcccact atcgtggtga ccatcctggc cgccctgggc     1740
ttcatcagta cgctggccat tctgctcatc ttctggagac atttccagac gcccatggtg     1800
cgctcggcgg gcggcccat gtgcttcctg atgctggtgc cctgctgct ggcgttcggg       1860 atggtccccg tgtatgtggg ccccccacg tcttctcct gtttctgccg ccaggctttc       1920
ttcaccgttt gcttctccgt ctgcctctcc tgcatcacgg tgcgctcctt ccagattgtg     1980
tgcgtcttca agatggccag acgcctgcca agcgcctacg gtttctggat gcgttaccac    2040
gggccctacg tcttcgtggc cttcatcacg gccgtcaagg tggccctggt ggcgggcaac    2100
atgctggcca ccaccatcaa ccccattggc cggaccgacc ccgatgaccc caatatcata    2160
atcctctcct gccaccctaa ctaccgcaac gggctactct tcaacaccag catggacttg    2220
ctgctgtccg tgctgggttt cagcttcgcg tacgtgggca aggaactgcc caccaactac    2280
aacgaagcca agttcatcac cctcagcatg accttctcct tcacctcctc catctccctc    2340
tgcacgttca tgtctgtcca cgatggcgtg ctggtcacca tcatggatct cctggtcact    2400
gtgctcaact ttctggccat cggcttgggg tactttggcc ccaaatgtta catgatcctt    2460
ttctacccgg agcgcaacac ttcagcttat ttcaatagca tgattcaggg ctacacgatg    2520
aggaagagct ag                                                        2532
```

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence:amino acid
      sequence encoded by degenerate primer used to
      amplify taste cell specific GPCR-B4

<400> SEQUENCE: 5

Ser Ala Gly Gly Pro Met Cys Phe Leu Met
 1               5                  10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence:amino acid
      sequence encoded by degenerate primer used to amplify taste cell specific GPCR-B4

<400> SEQUENCE: 6

Trp Met Arg Tyr His Gly Pro Tyr Val Phe
1               5                  10

<210> SEQ ID NO 7
<211> LENGTH: 669
<212> TYPE: PRT
<213> ORGANISM: Homo sapiens
<220> FEATURE:
<223> OTHER INFORMATION: human G-protein coupled receptor (GPCR) B4
      amino acid sequence

<400> SEQUENCE: 7

Ile Thr Tyr Ser Ala Ile Ser Asp Glu Leu Arg Asp Lys Val Arg Phe
1               5                   10                  15

Pro Ala Leu Leu Arg Thr Thr Pro Ser Ala Asp His His Val Glu Ala
            20                  25                  30

Met Val Gln Leu Met Leu His Phe Arg Trp Asn Trp Ile Ile Val Leu
        35                  40                  45

Val Ser Ser Asp Thr Tyr Gly Arg Asp Asn Gly Gln Leu Leu Gly Glu
    50                  55                  60

Arg Val Ala Arg Arg Asp Ile Cys Ile Ala Phe Gln Glu Thr Leu Pro
65                  70                  75                  80

Thr Leu Gln Pro Asn Gln Asn Met Thr Ser Glu Glu Arg Gln Arg Leu
                85                  90                  95

Val Thr Ile Val Asp Lys Leu Gln Gln Ser Thr Ala Arg Val Val Val
            100                 105                 110

Val Phe Ser Pro Asp Leu Thr Leu Tyr His Phe Phe Asn Glu Val Leu
        115                 120                 125

Arg Gln Asn Phe Thr Gly Ala Val Trp Ile Ala Ser Glu Ser Trp Ala
    130                 135                 140

Ile Asp Pro Val Leu His Asn Leu Thr Glu Leu Gly His Leu Gly Thr
145                 150                 155                 160

Phe Leu Gly Ile Thr Ile Gln Ser Val Pro Ile Pro Gly Phe Ser Glu
                165                 170                 175

Phe Arg Glu Trp Gly Pro Gln Ala Gly Pro Pro Pro Leu Ser Arg Thr
            180                 185                 190

Ser Gln Ser Tyr Thr Cys Asn Gln Glu Cys Asp Asn Cys Leu Asn Ala
        195                 200                 205

Thr Leu Ser Phe Asn Thr Ile Leu Arg Leu Ser Gly Glu Arg Val Val
    210                 215                 220

Tyr Ser Val Tyr Ser Ala Val Tyr Ala Val Ala His Ala Leu His Ser
225                 230                 235                 240

Leu Leu Gly Cys Asp Lys Ser Thr Cys Thr Lys Arg Val Val Tyr Pro
                245                 250                 255

Trp Gln Leu Leu Glu Glu Ile Trp Lys Val Asn Phe Thr Leu Leu Asp
            260                 265                 270

His Gln Ile Phe Phe Asp Pro Gln Gly Asp Val Ala Leu His Leu Glu
        275                 280                 285

Ile Val Gln Trp Gln Trp Asp Arg Ser Gln Asn Pro Phe Gln Ser Val
    290                 295                 300

Ala Ser Tyr Tyr Pro Leu Gln Arg Gln Leu Lys Asn Ile Lys Thr Ser
305                 310                 315                 320

Leu His Thr Val Asn Asn Thr Ile Pro Met Ser Met Cys Ser Lys Arg
                325                 330                 335

-continued

Cys Gln Ser Gly Gln Lys Lys Pro Val Gly Ile His Val Cys Cys
            340                 345                 350

Phe Glu Cys Ile Asp Cys Leu Pro Gly Thr Phe Leu Asn His Thr Glu
        355                 360                 365

Cys Pro Asn Asn Glu Trp Ser Tyr Gln Ser Glu Thr Ser Cys Phe Lys
370                 375                 380

Arg Gln Leu Val Phe Leu Glu Trp His Glu Ala Pro Thr Ile Ala Val
385                 390                 395                 400

Ala Leu Leu Ala Ala Leu Gly Phe Leu Ser Thr Leu Ala Ile Leu Val
                405                 410                 415

Ile Phe Trp Arg His Phe Gln Thr Pro Ile Val Arg Ser Ala Gly Gly
            420                 425                 430

Pro Met Cys Phe Leu Met Leu Thr Leu Leu Leu Val Ala Tyr Met Val
        435                 440                 445

Val Pro Val Tyr Val Gly Pro Pro Lys Val Ser Thr Cys Leu Cys Arg
450                 455                 460

Gln Ala Leu Phe Pro Leu Cys Phe Thr Ile Cys Ile Ser Cys Ile Ala
465                 470                 475                 480

Val Arg Ser Phe Gln Ile Val Cys Ala Phe Lys Met Ala Ser Arg Phe
                485                 490                 495

Pro Arg Ala Tyr Ser Tyr Trp Val Arg Tyr Gln Gly Pro Tyr Val Ser
            500                 505                 510

Met Ala Phe Ile Thr Val Leu Lys Met Val Ile Val Val Ile Gly Met
        515                 520                 525

Leu Ala Arg Pro Gln Ser His Pro Arg Thr Asp Pro Asp Asp Pro Lys
530                 535                 540

Ile Thr Ile Val Ser Cys Asn Pro Asn Tyr Arg Asn Ser Leu Leu Phe
545                 550                 555                 560

Asn Thr Ser Leu Asp Leu Leu Leu Ser Val Val Gly Phe Ser Phe Ala
                565                 570                 575

Tyr Met Gly Lys Glu Leu Pro Thr Asn Tyr Asn Glu Ala Lys Phe Ile
            580                 585                 590

Thr Leu Ser Met Thr Phe Tyr Phe Thr Ser Ser Val Ser Leu Cys Thr
        595                 600                 605

Phe Met Ser Ala Tyr Ser Gly Val Leu Val Thr Ile Val Asp Leu Leu
610                 615                 620

Val Thr Val Leu Asn Leu Leu Ala Ile Ser Leu Gly Tyr Phe Gly Pro
625                 630                 635                 640

Lys Cys Tyr Met Ile Leu Phe Tyr Pro Glu Arg Asn Thr Pro Ala Tyr
                645                 650                 655

Phe Asn Ser Met Ile Gln Gly Tyr Thr Met Arg Arg Asp
            660                 665

<210> SEQ ID NO 8
<211> LENGTH: 2010
<212> TYPE: DNA
<213> ORGANISM: Homo sapiens
<220> FEATURE:
<223> OTHER INFORMATION: human G-protein coupled receptor (GPCR) B4
      nucleotide sequence

<400> SEQUENCE: 8
atcacctaca gcgccatcag cgatgagctg cgagacaagg tgcgcttccc ggctttgctg    60
cgtaccacac ccagcgccga ccaccacgtc gaggccatgg tgcagctgat gctgcacttc   120
cgctggaact ggatcattgt gctggtgagc agcgacacct atggccgcga caatggccag   180

```
ctgcttggcg agcgcgtggc ccggcgcgac atctgcatcg ccttccagga gacgctgccc    240
acactgcagc ccaaccagaa catgacgtca gaggagcgcc agcgcctggt gaccattgtg    300
gacaagctgc agcagagcac agcgcgcgtc gtggtcgtgt tctcgcccga cctgaccctg    360
taccacttct tcaatgaggt gctgcgccag aacttcacgg gcgccgtgtg gatcgcctcc    420
gagtcctggg ccatcgaccc ggtcctgcac aacctcacgg agctgggcca cttgggcacc    480
ttcctgggca tcaccatcca gagcgtgccc atcccgggct tcagtgagtt ccgcgagtgg    540
ggcccacagg ctgggccgcc acccctcagc aggaccagcc agagctatac ctgcaaccag    600
gagtgcgaca actgcctgaa cgccaccttg tccttcaaca ccattctcag gctctctggg    660
gagcgtgtcg tctacagcgt gtactctgcg gtctatgctg tggcccatgc cctgcacagc    720
ctcctcggct gtgacaaaag cacctgcacc aagagggtgg tctaccccctg gcagctgctt    780 gaggagatct ggaaggtcaa cttcactctc ctggaccacc aaatcttctt cgacccgcaa    840
ggggacgtgg ctctgcactt ggagattgtc cagtggcaat gggaccggag ccagaatccc    900
ttccagagcg tcgcctccta ctaccccctg cagcgacagc tgaagaacat caagacatct    960
ctgcacaccg tcaacaacac gatccctatg tccatgtgtt ccaagaggtg ccagtcaggg    1020
caaaagaaga agcctgtggg catccacgtc tgctgcttcg agtgcatcga ctgccttccc    1080
ggcaccttcc tcaaccacac tgaatgcccg aataacgagt ggtcctacca gagtgagacc    1140
tcctgcttca gcggcagct ggtcttcctg gaatggcatg aggcacccac catcgctgtg    1200
gccctgctgg ccgccctggg cttcctcagc accctggcca tcctggtgat attctggagg    1260
cacttccaga cacccatagt tcgctcggct gggggcccca tgtgcttcct gatgctgaca    1320
ctgctgctgt ggcatacat ggtggtcccg gtgtacgtgg ggccgcccaa ggtctccacc    1380
tgcctctgcc gccaggccct cttcccctc tgcttcacaa tttgcatctc ctgtatcgcc    1440
gtgcgttctt tccagatcgt ctgcgccttc aagatggcca gccgcttccc acgcgcctac    1500
agctactggg tccgctacca ggggccctac gtctctatgg catttatcac ggtactcaaa    1560
atggtcattg tggtaattgg catgctggca cggcctcagt cccaccccg tactgacccc    1620 gatgacccca agatcacaat tgtctcctgt aaccccaact accgcaacag cctgctgttc    1680
aacaccagcc tggacctgct gctctcagtg gtgggtttca gcttcgccta catgggcaaa    1740
gagctgccca ccaactacaa cgaggccaag ttcatcaccc tcagcatgac cttctatttc    1800
acctcatccg tctccctctg caccttcatg tctgcctaca gcggggtgct ggtcaccatc    1860
gtggacctct tggtcactgt gctcaacctc ctggccatca gcctgggcta cttcggcccc    1920
aagtgctaca tgatcctctt ctaccccgag cgcaacacgc ccgcctactt caacagcatg    1980
atccagggct acaccatgag gagggactag                                     2010
```

<210> SEQ ID NO 9  
<211> LENGTH: 6  
<212> TYPE: PRT  
<213> ORGANISM: Artificial Sequence  
<220> FEATURE:  
<223> OTHER INFORMATION: Description of Artificial Sequence:amino acid sequence encoded by degenerate primers used for PCR amplification of motifs highly conserved among the area between transmembrane domains 6 and 7 of VR/mGluR/CaST/GPCR-B3 receptors  
<220> FEATURE:  
<221> NAME/KEY: MOD_RES  
<222> LOCATION: (1)  
<223> OTHER INFORMATION: Xaa = Tyr or Asn

<400> SEQUENCE: 9

```
Xaa Phe Asn Glu Ala Lys
  1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence:amino acid
      sequence encoded by degenerate primers used for
      PCR amplification of motifs highly conserved among
      the area between transmembrane domains 6 and 7 of
      VR/mGluR/CaST/GPCR-B3 receptors
<220> FEATURE:
<221> NAME/KEY: MOD_RES
<222> LOCATION: (5)
<223> OTHER INFORMATION: Xaa = Ile or Val

<400> SEQUENCE: 10

Pro Lys Cys Tyr Xaa Ile
  1               5
```